(12) United States Patent
Miller

(10) Patent No.: US 6,442,440 B1
(45) Date of Patent: Aug. 27, 2002

(54) COMPUTER INTERFACE MODULE HAVING A FLAT MENU

(75) Inventor: Kerry Lynn Miller, Elkton, MD (US)

(73) Assignee: Dade Behring Inc., Deerfield, IL (US)

( * ) Notice: Subject to any disclaimer, the term of this patent is extended or adjusted under 35 U.S.C. 154(b) by 77 days.

(21) Appl. No.: 09/602,695

(22) Filed: Jun. 24, 2000

(51) Int. Cl.⁷ .............................................. G05B 15/00
(52) U.S. Cl. ........................................ 700/83; 345/965
(58) Field of Search .............................. 700/17, 83, 84, 700/266; 345/961, 965, 970; 436/43, 55, 166; 422/50, 62, 63, 119; 128/922; 73/863, 863.01

(56) References Cited

U.S. PATENT DOCUMENTS

| | | | |
|---|---|---|---|
| 5,316,726 A | 5/1994 | Babson et al. ................. 422/65 |
| 5,437,838 A | 8/1995 | DeMoranville et al. ........ 422/67 |
| 5,482,861 A | 1/1996 | Clark et al. .................... 436/48 |
| 5,631,844 A | * 5/1997 | Margrey et al. ............ 700/266 |
| 5,879,629 A | 3/1999 | Ridgeway et al. ............ 422/73 |
| 5,885,530 A | 3/1999 | Babson et al. ................. 422/65 |
| 5,985,672 A | 11/1999 | Kegelman et al. ............ 436/50 |
| 6,058,764 A | 5/2000 | Yamada et al. ............. 73/61.52 |

FOREIGN PATENT DOCUMENTS

| | | |
|---|---|---|
| EP | 0 851 232 | 7/1998 |
| EP | 1 087 231 | 3/2001 |

* cited by examiner

Primary Examiner—Paul P. Gordon
(74) Attorney, Agent, or Firm—Leland K. Jordan

(57) ABSTRACT

A computer interface module having a first information display screen that is directly linked to a plurality of additional information display screens containing on-line information about the operational status of plurality of interrelated automated devices as well as information describing the location of any specific sample and the status of clinical tests to be performed on the sample. A combination of general function buttons and specific function buttons as well as a scrollable text area where informational messages are displayed.

14 Claims, 23 Drawing Sheets

COMPUTER INTERFACE MODULE HAVING A FLAT MENU

FIELD OF THE INVENTION

The present invention relates to automated clinical analyzers having the ability to provide multiple assay versatility and flexibility, and more particularly, to a method for controlling the operation of the plurality of interrelated automated analytical and sample preparation devices and for obtaining information about the status of a given sample or device.

BACKGROUND OF THE INVENTION

Clinical diagnostic analyzers are being developed with increasing levels of complexity and sophistication in order to fully automated the performance of chemical assays and immunoassays of biological fluids such as urine, blood serum, plasma, cerebrospinal liquids and the like. Generally, reactions between an analyte in a patient sample and reagents used during the assay result in generating some sort of signal that can be measured by the analyzer. From this signal the concentration of a analyte in the patient sample may be calculated.

In addition to automation, there is increased emphasis on the capability of an analyzer to provide multiple assay versatility and flexibility and at the same time reducing demand on the skills of the operating technician to perform complex programming and scheduling of assays or other analyzer functions. At the same time, modern clinical analyzers must be more cost and performance effective in terms of operating costs, turnaround time of test results, maintenance, operator training, etc. Thus, during the operation of such an analyzer, it is often critical for a technician to be able to easily and quickly obtain particular information about the assay status of a given sample among a large number of sample also being assayed, the quality performance of an analyzer, and generally be able to access a vast amount of information helpful in providing clinical diagnosis to a patient.

U.S. Pat. No. 6,058,764 discloses an analytical apparatus which can produce an analytical value on the basis of data entered during manual sample preparation which can be easily traced and used editing of the analytical result of the analyzer. The analytical apparatus has an input device for inputting sample preparation procedures through a display screen, and various computations based on weighed quantities, and constant dilution volume are automatically entered during the manual preparation as to eliminate human error.

U.S. Pat. No. 5,885,530 describes a high throughput automated immunoassay system which can perform high volume testing on a broad range of analytes while selecting from among a diverse set of immunoassays for any given sample. The immunoanalyzer has the capacity to perform a wide range of different types of immunoassays by facile storage and automated combination aboard the or analyzer among a wide variety of different types of reagents and heterogenous immunoassay beads stored on-board the analyzer. The automated design allows reduced user interface (e.g., tests are performed automatically from computer input) including the ability to order, perform and reassay tests reflexively based on test results without operator intervention.

U.S. Pat. No. 5,482,861 is typical of modern analyzers and discloses a typical modern automated analyzer providing continuous and random access analysis, having apparatus and methodology capable of simultaneously performing multiple assays of liquid samples using different assay methodologies. A method is also disclosed of operating an automated continuous and random access analytical system capable of simultaneously effecting multiple assays of a plurality of liquid samples wherein scheduling of various assays of the plurality of liquid samples is followed by creating a unit do disposable and separately transferring a first liquid sample and reagents to a reaction vessel without initiation of an assay reaction sequence, followed by physical transfer of the unit dose disposable to a processing device, whereby a mixture of the unit dose disposable reagents and sample are achieved during incubation.

U.S. Pat. No. 5,437,838 discloses a multi-tasking clinical laboratory work-flow system for test sample an reagent transfer to semi-automate various laboratory assays. The system includes a controller having a menu of protocols which provide format instructions to a robotic sample transfer device. The sample transfer device includes a work-flow surface having defined coordinates for mounting one or more test racks and one or more reaction mediums, and means for interacting a test sample with one or more reagent(s) or gel in a reaction medium.

U.S. Pat. No. 5,316,726 discloses an automated immunoassay analyzer includes a computer controlled instrument and display. The display provides a real-time presentation of all operations being performed within the instrument. A large number of samples can be loaded into the instrument, and the order of testing the samples can be rearranged according to a priority determined by the operator at any time. A variety of immunoassays can be performed on each sample and different immunoassays can be performed on any one sample. Information related to the type of immunoassays being performed on particular samples is collected by a bar code reader and this information is conveyed to the computer for presentation on the display. The computer tracks the progress of each immunoassay through the reaction circuit to the detection device. The time to completion for particular immunoassays as well as the concentration information for recently completed immunoassays is provided.

Such prior art analyzer interface modules are increasingly unsatisfactory as the degree of analyzer complex and automation increases. For example, many known systems for controlling an analyzer depend simply inputting the assays desired to be completed and do not allow for handling of special informational messages about the samples being analyzer or maintenance of the analyzer. In addition, it is becoming necessary to couple one or more analyzers to one or more sample preparation devices adapted to automatically perform special sample preparation operations like sample identification, aliquotting, dilution, centrifugation, etc, before a sample is presented to an analyzer for analysis. In such instances, the need for controlling the operation of the plurality of interrelated automated devices and for obtaining information about the status of a given sample or automated device exceeds the abilities of known clinical system control and information display modules Accordingly, as the state of the art advances and more demands are made on the analyzer's control and display systems there is a continuing need for a simple and rapid method to easily provide control and information display modules that are capable of rapidly determining information defining the overall status of the analytical system without an undue amount of operator training or effort obtain the needed information. It is particularly desirable to operate such an improved module without recourse to hand-held mouse-like input devices that consume valuable space in a clinical analytical system.

SUMMARY OF THE INVENTION

It is therefore an object of this invention to provide a computer interface module that allows for a user to easily and quickly access a variety of control screens and status information display screens that full describe a plurality of interrelated automated devices used for sample preparation and clinical analysis of a patient's biological sample. This and other advantages are accomplished in accordance with the invention by providing a computer interface module having a first information display screen that is directly linked to a plurality of additional information display screens containing on-line information out the operational status of plurality of interrelated automated devices as well as information describing the location of any specific sample and the status of clinical tests to be performed on the sample. The computer interface display module is thus adapted to facilitate interactions between an operator and an automated clinical analytical system wherein the module comprises a visual touch screen adapted to display a menu including icons, scroll bars, boxes and buttons through which the operator may interface with the clinical analytical system and wherein the menu comprises a number of function buttons programmed to display functional aspects of the clinical analytical system. The computer interface further comprises a number of function specific buttons programmed to display detailed functional aspects for each function button so that additional information about the status and performance of the clinical analytical system may be displayed by activating no more than two of said function buttons and function specific buttons. The unique design of the computer interface module and its interface with a clinical laboratory's patient and operating database allows an operator to access nearly all important information screens using such a flat menu where only two screens are activated whereby the need for a simple and rapid method to easily display information defining the overall status of the analytical system is achieved.

BRIEF DESCRIPTION OF THE DRAWINGS

For a better understanding of the invention as well as other objects and further features thereof, reference made to the following detailed description of various preferred embodiments thereof, taken in connection with the accompanying drawings wherein.

DETAILED DESCRIPTION OF THE PREFERRED EMBODIMENTS

Figure 1:
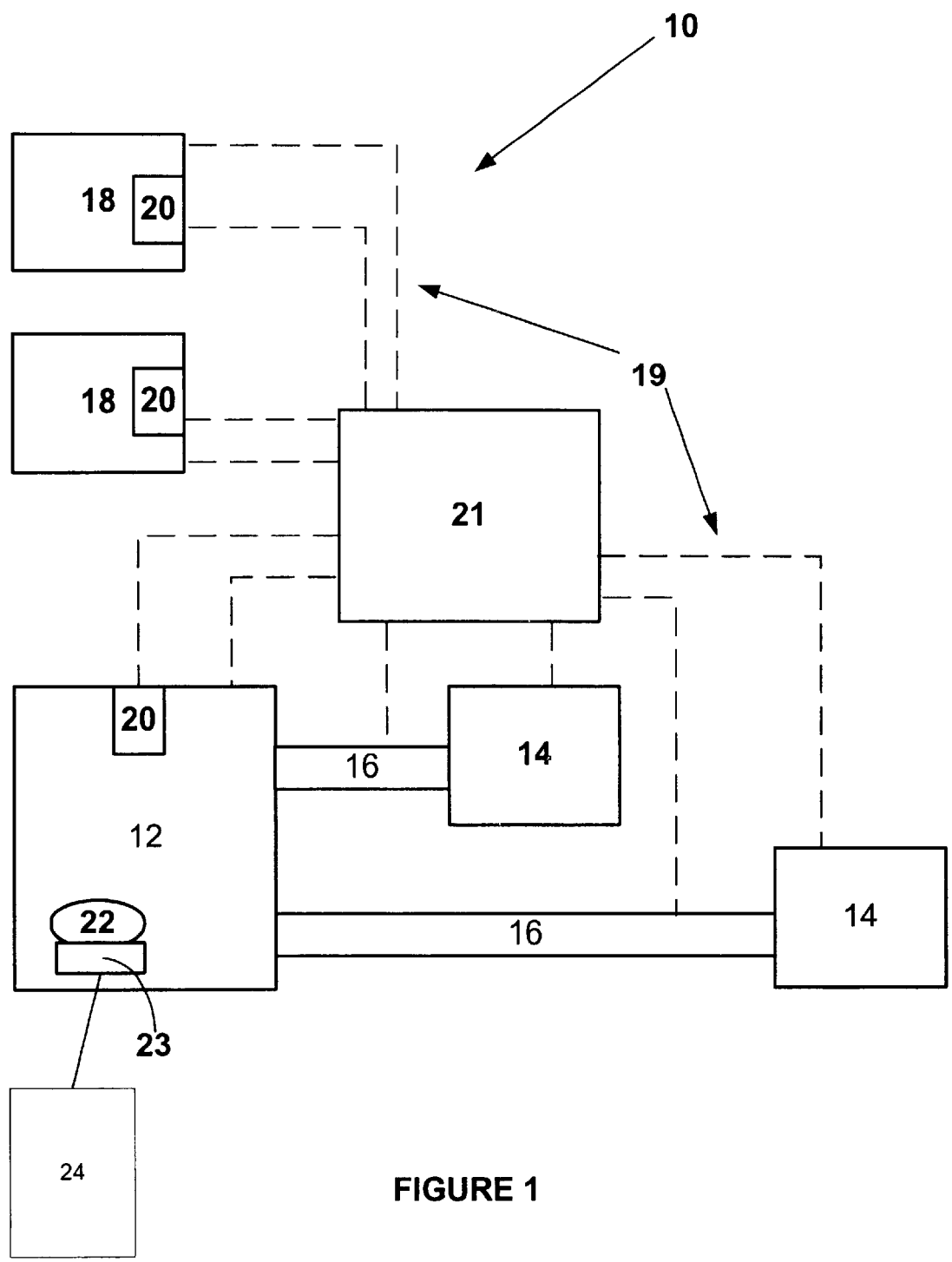
FIG. 1 is schematic representation of an clinical analytical system in which the present invention may be practiced.

Referring to FIG. 1, there is illustrated a clinical analytical system 10 in which the present invention maybe utilized to advantage. The clinical analytical system 10 includes at least one clinical analyzer 12 adapted to perform chemical assays and immunoassays on samples of biological fluids such as urine, blood serum, plasma, cerebrospinal liquids and the like. Such analyzers are well known in the art, being described, for example, in U.S. Pat. No. 5,985,672 and 5,482,861. Prior to analysis of such biological samples, it is common to automatically or semi-automatically carry out such sample preparation operations as decapping of a closed sample tube, aliquotting of portions of samples from a primary tube to a secondary tube, sample identification, dilution, centrifugation, etc, in order to prepare the original biological sample for analysis by analyzer 12. The clinical analytical system 10 is shown as including two of such automated sample preparation devices, including r example a first sample preparation device 14 that is adapted to perform the required sample preparation operations and present individual open sample test tubes to analyzer 12 using a mechanized sample tube transfer means 16 like those known in the art. A second sample preparation device 18 is also shown, the second preparation device 18 being adapted to perform the same required sample preparation operations and prepare a rack 20 of individual open sample test tubes that may be carried to analyzer 12 by a technician. Although two such sample handlers 14 and 18 are shown for the purpose of describing the clinical analytical system 10, it will be apparent to those skilled in the art that any number of sample handling systems may be present in an clinical analytical system 10. Similarly, although only one analyzer 12 is shown for the purpose of describing the clinical analytical system 10, it will be apparent to those skilled in the art that any number of clinical a ay be present in an clinical analytical system 10. Such automated clinical analyzers 12 are well known in the art and those skilled in the art know with certainty the functions of the elements the analyzers to which reference is made hereinafter. In particular, clinical analyzers 12 are typically equipped with a on-board computer system 22 including a CPU and appropriate memory programmed to control all operating, testing and reporting, maintenance, inventory control, etc., aspects of the analyzer 12. Interactions between the CPU and a technician are conventionally accomplished by inputting data and/or instructions and/or requests for information residing within the computer system 22 using a keyboard 23 or a number of touch-buttons display on a visual computer interface screen or module 24. Conventional electronic drivers and interface circuits are used to interface the various electro-mechanical devices, sensors and controls, etc. within analyzer 12 to computer system 22. The computer system 22 and all other components within the clinical analytical system 10 are furthermore linked as indicated by dashed lines 19 to a clinical laboratory's Laboratory Information System 21 (LIS, hereinafter), a database of information containing comprehensive information about patients in a hospital or laboratory, the testing devices within the hospital, clinical test and facility schedules, inventor levels, billing, hospital staff scheduling, etc. LIS systems are well known and employed in the majority of larger clinical laboratories.

Figure 2:
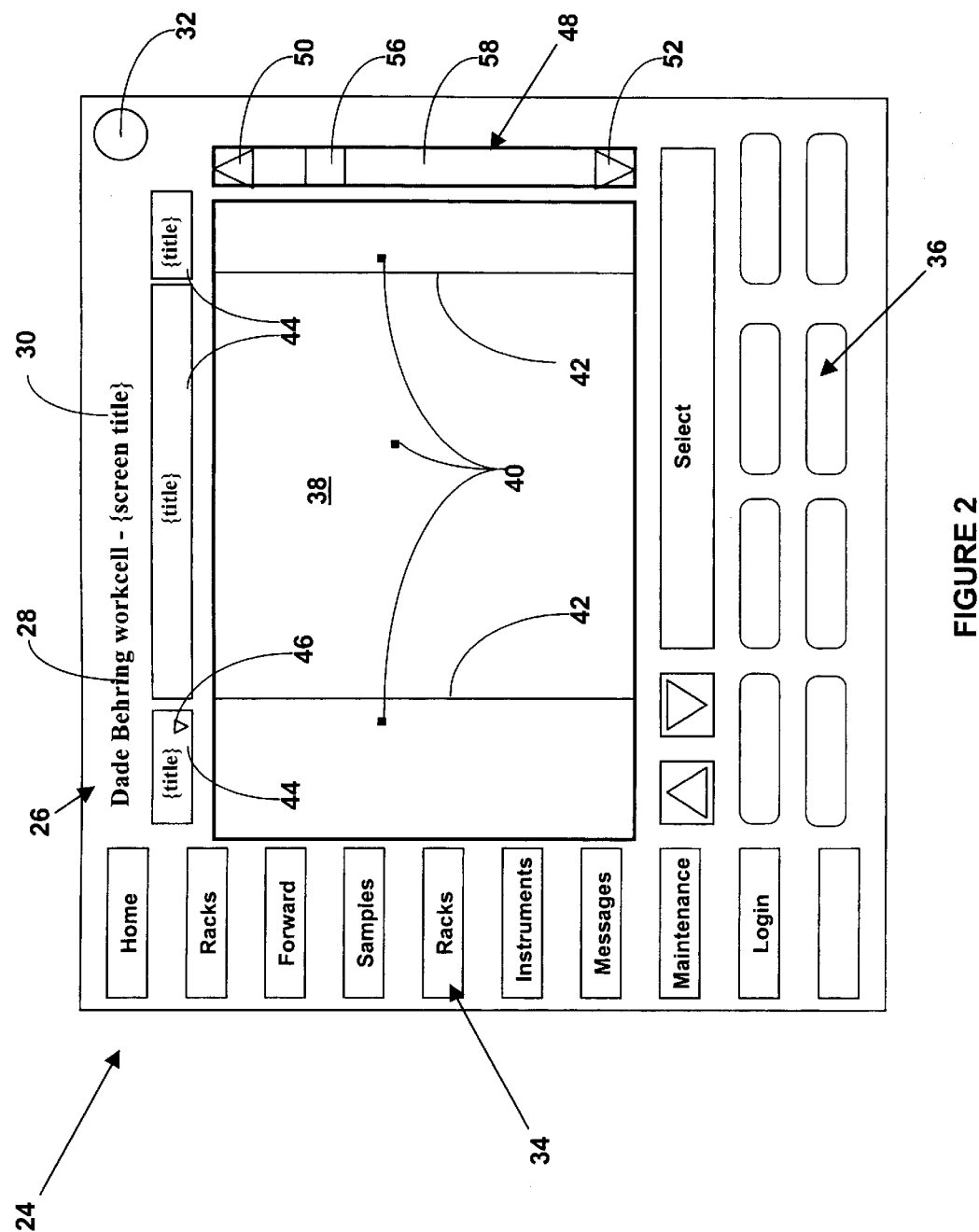
FIG. 2 is a typical representation of an initial computer interface module information display screen exemplary of the present invention.

FIG. 2 shows a computer interface display or module (CIM) 24 illustrative of the present invention. In a particularly illustrative embodiment, CIM 24 comprises a visual touch screen 24 for user input and information display displaying a number of icons, scroll bars, boxes or buttons through which an operator may interface with the clinical system 10 and the LIS 21 to interrogate or supply data. Touch screens like the ones employed in practicing the present invention are commercially available and their operation and interconnection with the other devices including computer system 22 and LIS 21 are known in the art. Throughout the disclosure of the present invention several terms known in the art are used to indicate an interaction between an operator or technician and the CIM 24; phrases such as "activating a button", "pressing a button", "touching a button" are generally intended to indicate any of several methods to select an given area of the display or screen portion of CIM 24. To insure a consistent interface all screens should share some common attributes including a title bar 26 that indicates the system name 28 (for example, Dade Behring workcell) and the screen title 30 of the specific screen being displayed. The location of the Title Bar 26 is at the top and center of the CIM 24. The font, size and color of the title bar content will be the same for every screen displayed by CIM 24. Each CIM 24 screen will display a status icon 32 in the top right hand corner of the screen to indicate the summary status of the clinical analytical system 10. The status icon 32 as displayed will change color and shape to properly indicate overall clinical analytical system 10 status. This icon will appear, for example as a Round Green icon for proper functioning of system 19, as a Triangular Yellow icon for warning that some of clinical analytical system's 10 component(s) need attention but system 10 continues to operate, and as a Hexagonal Red icon for errors that will or have already shut down operation of clinical analytical system 10.

All screens have a standard set of general function buttons 34 to provide the user with express navigation controls. These function buttons 34 are located from top to bottom along the left edge of the screen and are named to indicate their function.

When one of these buttons 34 are pressed, the button 34 will change color and stay changed until another system function button is pressed. The Back, Forward and Login buttons are preferably exceptions and do not change color or affect the color of any other system function button 34. Login will change color when a popup keypad described hereinafter is displayed but will not cause any other system function button to change color. When the clinical analytical system 10 first begins operation, the Home button color state is as if it had been pressed.

The operation of CIM 24 as a consequence of pressing each of the function buttons 34 is as follows:

Pressing the function button 34 marked "Home" will cause the System Status screen to be displayed.

Pressing the function button 34 marked "Back" will cause CIM 24 to back up to previously selected screen. This button is to work exactly like the Back button on most web browsers. Example: If user in the Samples screen then selects a sample to move to the Sample Details screen, pressing the Back button in the Sample Details screen will take the user back to the same Samples screen they were in before entering the Sample Detail screen.

Pressing the function button 34 marked "Forward" will cause CIM 24 to revisit previously selected screen. This button is to work exactly like the Forward button on most web browsers. Example: If the user had traversed from a Samples screen to a Sample Details screen then "Back" to the Samples screen as described above (Back), pressing the Forward button would take the user to Sample Details Screen they had previously visited.

Pressing the function button 34 marked "Samples" will cause the default Samples Screen to be displayed.

Pressing the function button 34 marked "Racks" will cause the default Racks Screen to be displayed.

Pressing the function button 34 marked "Instruments" will cause the default Instruments Screen to be displayed.

Pressing the function button 34 marked "Messages" will cause the default Messages Screen to be displayed.

Pressing the function button 34 marked "Maintenance" will cause the default Maintenance Selection Screen to be displayed.

Pressing the function button 34 marked "Login" will cause the Login popup keyboard to be displayed over the current screen being displayed.

An unmarked, unassigned system function button may be included and reserved for future use.

Each screen in CIM 24 also includes has provisions for eight screen function specific buttons 36 that are specific to the screen being displayed. Button functionality is specific to the screen. The function specific buttons 36 are preferably located in two rows of four at the bottom of the screen and biased to the right.

The assignment of these screen function specific buttons 36 is generally variable except that recurring function buttons (such as search, print, etc . . . ) are positioned to coincide with all other screens that use these common functions. The intent of this is to provide a consistent button placement for the user.

As shown computer system 20 and CIM 22 include a scrolled area 38 to present detailed information about each of the buttons 34 or 36. Discrete columns 40 in a scrolled area have a thin vertical line 42 to separate the columns.

Each column 40 in a scrolled area 38 preferably has a Column Heading button 44 associated and aligned with the column 40. The button is tri-state to indicate column 40 is not sorted or is sorted in ascending or descending order. A small triangle 46 in the bottom right hand corner of the button 44 indicate this state or order. A down pointing triangle is used to indicate a descending sort; an up pointing triangle is used to indicate ascending sort; and no triangle is used to indicate an unsorted column 40. Only one column 40 can control the sorting of rows. Each display screen will have a default sort column (ascending or descending order), as shown for the leftmost column 40 in FIG. 2.

Pressing a Column Heading Button 44 that is the active sort column will toggle its ascending/descending state and cause a redisplay of the scrolled area reflecting the new sorted order. If a row was highlighted (i.e. selected) the redisplayed screen will always continue to contain the highlighted row.

Pressing a Column Heading Button 44 that is not the active sort column will cause it to be the new so column in descending order and cause a redisplay of the scrolled area reflecting the new sorted order. If a row was highlighted (i.e. selected) the redisplay will continue to contain the highlighted row. The previously active sort column will now indicate that it is not active for sorting.

A standard roll control panel 48 is located to the right of the scroll area 38 and operates and controls much like typical web browser controls. Pressing the up arrow 50 scrolls up (i.e. moves text down) one line at a time. Pressing the down arrow 52 scrolls down (i.e. moves text up) one line at a time. Pressing the background 58 between the up arrow and the dark gray square button 56 scrolls up one page at a time and pressing the background 58 between the down arrow 52 and the dark gray square button 56 scrolls down one page at a time. Touching and dragging the dark gray button 56 up or down moves the scroll area 38 view appropriately.

Figure 3:
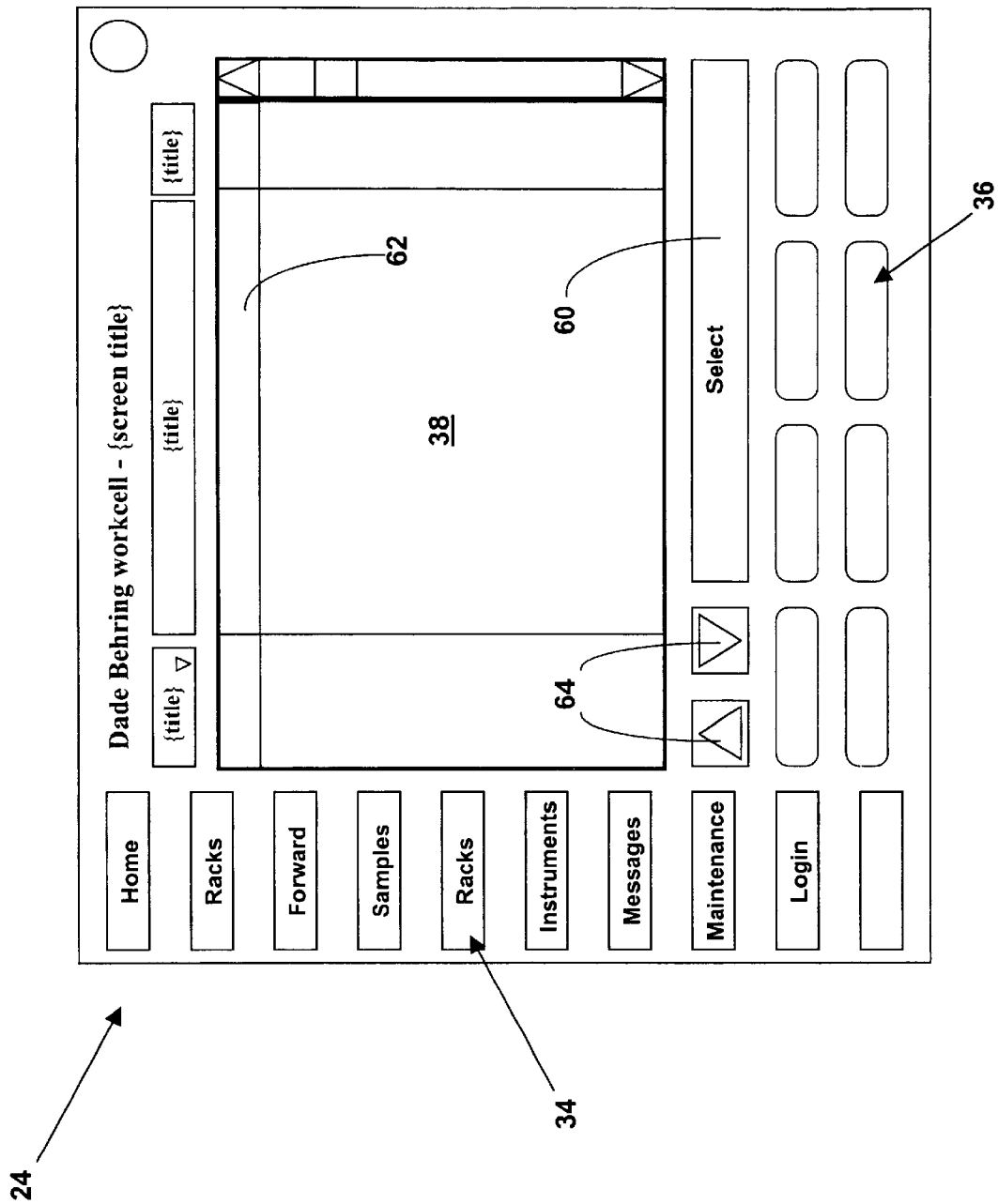
FIG. 3 is typical representation of the computer interface module information display screen of FIG. 2 further illustrating Selection Control Buttons exemplary of the present invention.

As seen in FIG. 3, below the scroll area are Selection Control Buttons 60 to assist the user in highlighting and selecting rows 62 in a scrolled area (only one row 62 is shown for purposes of clarity). Because the scroll area 38 is a touch screen it is often difficult to highlight and/or select densely packed features on the screen.

To highlight a row 62 in a scrolled area 38 the user can touch the row 62 within the scrolled area 38 and/or use the selection control buttons 60. If desired row 62 is highlighted after pressing the scrolled area 38 the user can select the row 62 by pressing or activating or touching the Select button 60. If the wrong row 62 was highlighted, the user can use the Up and Down selection control arrows 64 to move the highlighted line to the desired row 62. Then to select the row "double press" the Select button 60.

Alternatively, a technician or other user could use the Select button 60 to highlight a non-selected row and then use the Up and Down arrow buttons 64 to move the highlighted line to the desired row 62. Selection of the row 62 would then be the same as described above.

When a row 62 is highlighted the selection control Up and Down arrow buttons 64 cause the following behavior. The highlighted line 62 will never enter the first three rows of the scroll area when there is the possibility to scroll up the display. Only when the first item of the list corresponds with the first line of the display will the highlighted line be allowed on lines 3, 2, or 1. Conversely, the highlighted line 62 will never enter the last three rows of the scrolled area when there is the possibility to scroll down. This highlighted scroll behavior is intended to always allow the user to see three items before and after the highlighted line making it easier to select the desired row 62.

Figure 4A:
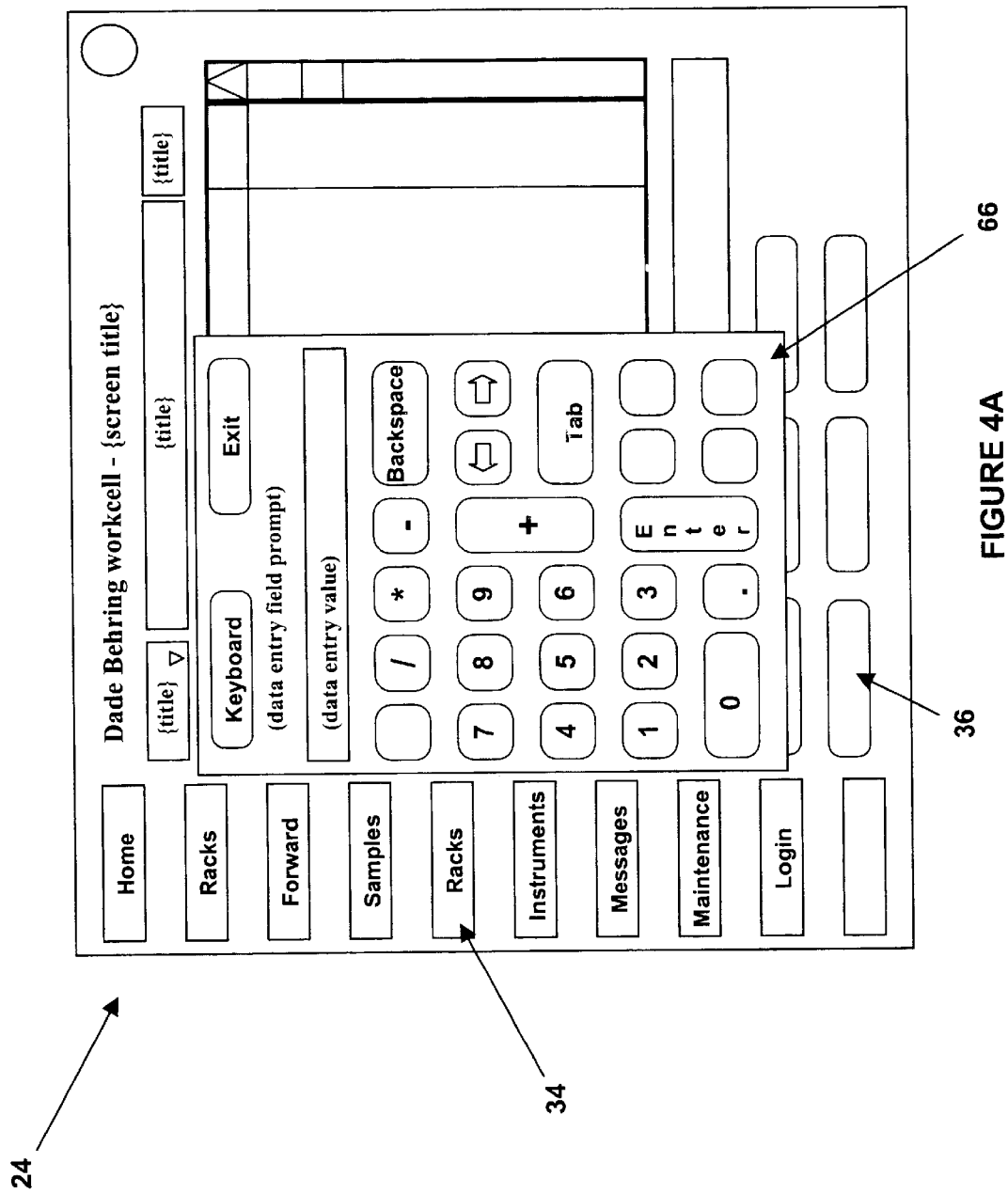
FIG. 4A is a typical representation of the computer interface module information display screen of FIG. 2 further illustrating a Popup Keyboard in a keyboard style layout exemplary of the present invention.
Figure 4B:
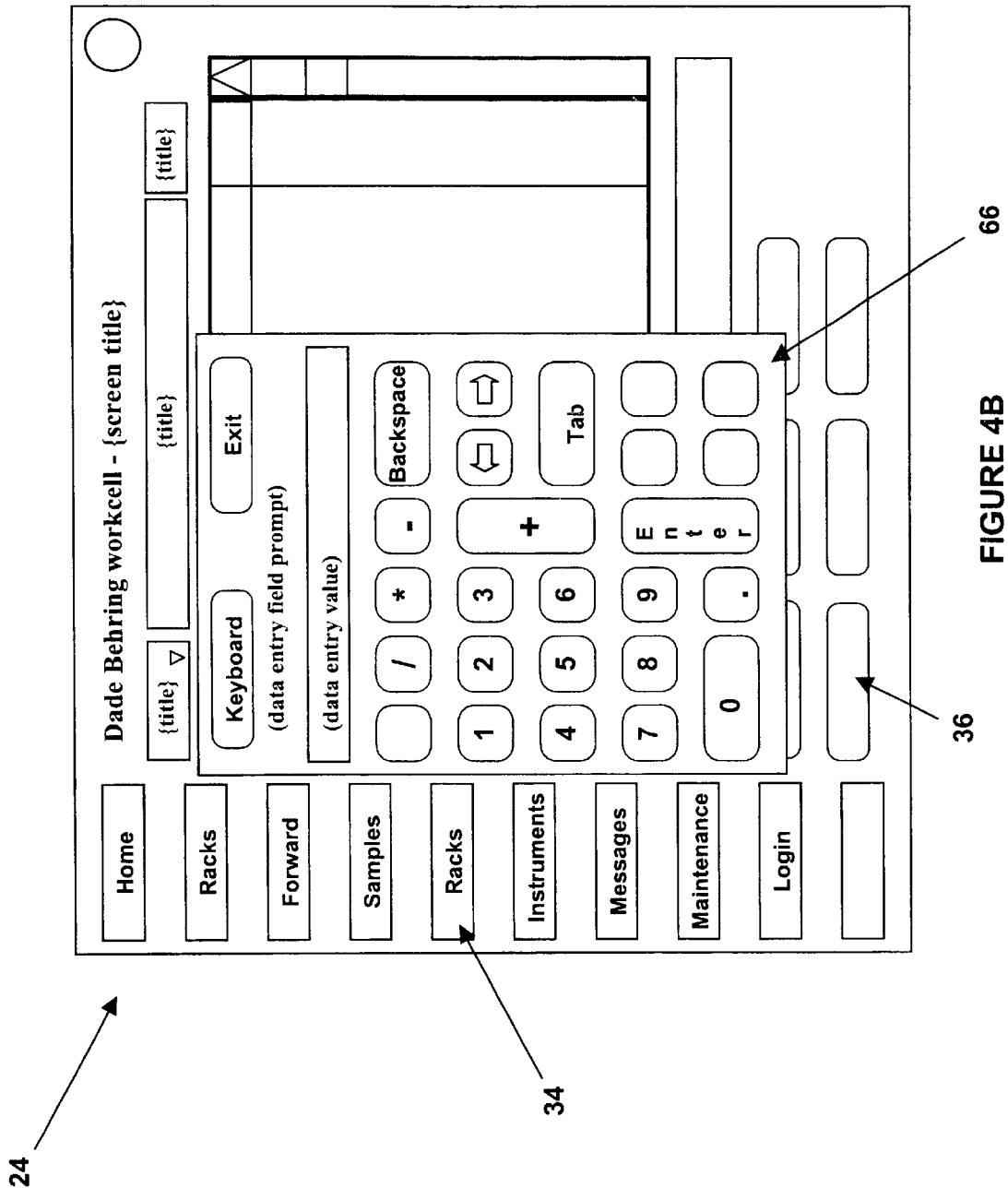
FIG. 4B is a typical representation of the computer interface module information display screen of FIG. 2 further illustrating a Popup Keyboard in a phone style layout exemplary of the present invention.

When a line 62 is not highlighted the selection control Up and Down arrow buttons 64 should act exactly like the up and down scroll buttons described in the previous section. As seen in FIG. 4A and 4B, most use inputs are likely to be accommodated by system function buttons 34 or by screen function specific buttons 36 or by selection from a scrollable list. In the event that numeric or alphanumeric data entry is required a popup keyboard 66 is provided to facilitate user data entry via the CIM 24. If the data to be entered are numeric only a numeric keyboard 66 is used for user input. The user can select from either of two similarly performing numeric keyboard layouts, a keypad-like layout 66 as shown in FIG. 4A, or a phone-style layout 68 as shown in FIG. 4B. When the Keyboard button is pressed the keyboard layout toggles.

Figure 5A:
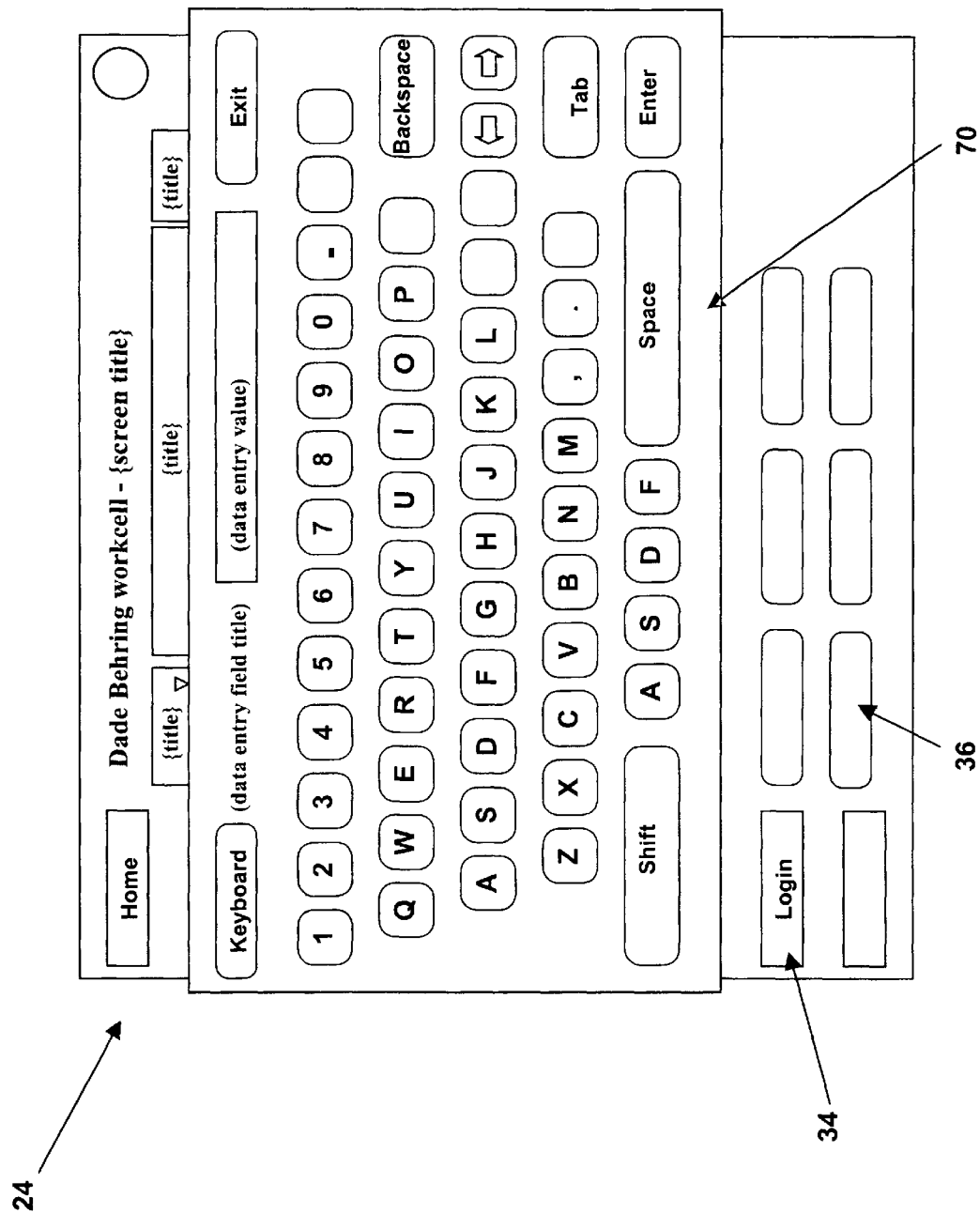
FIG. 5A is a typical representation of the computer interface module information display screen of FIG. 2 further illustrating a QWERT Keyboard exemplary of the present invention.
Figure 5B:
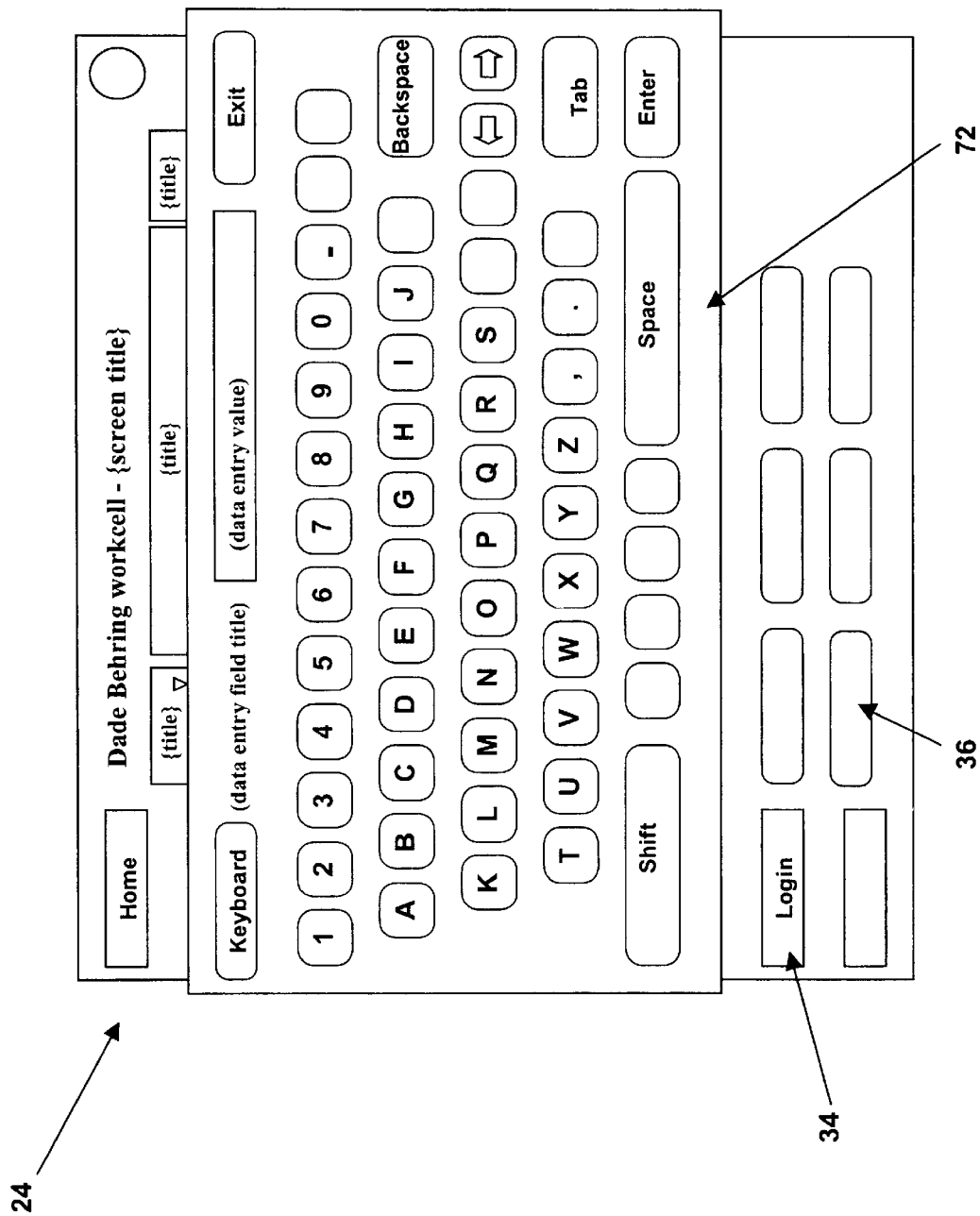
FIG. 5B is a typical representation of the computer interface module information display screen of FIG. 2 further illustrating an Alphanumeric Keyboard exemplary of the present invention.

If the data to be entered require alphanumeric input, a full alphanumeric keyboard is provided for user input. The user can select from two alphanumeric keyboard layouts (QWERT layout 70 as seen in FIG. 5A and alphabetic layout 72 as seen in FIG. 5B). When the Keyboard button is pressed the keyboard layout toggles. The alphanumeric keyboard is language specific in its layout.

Figure 6:
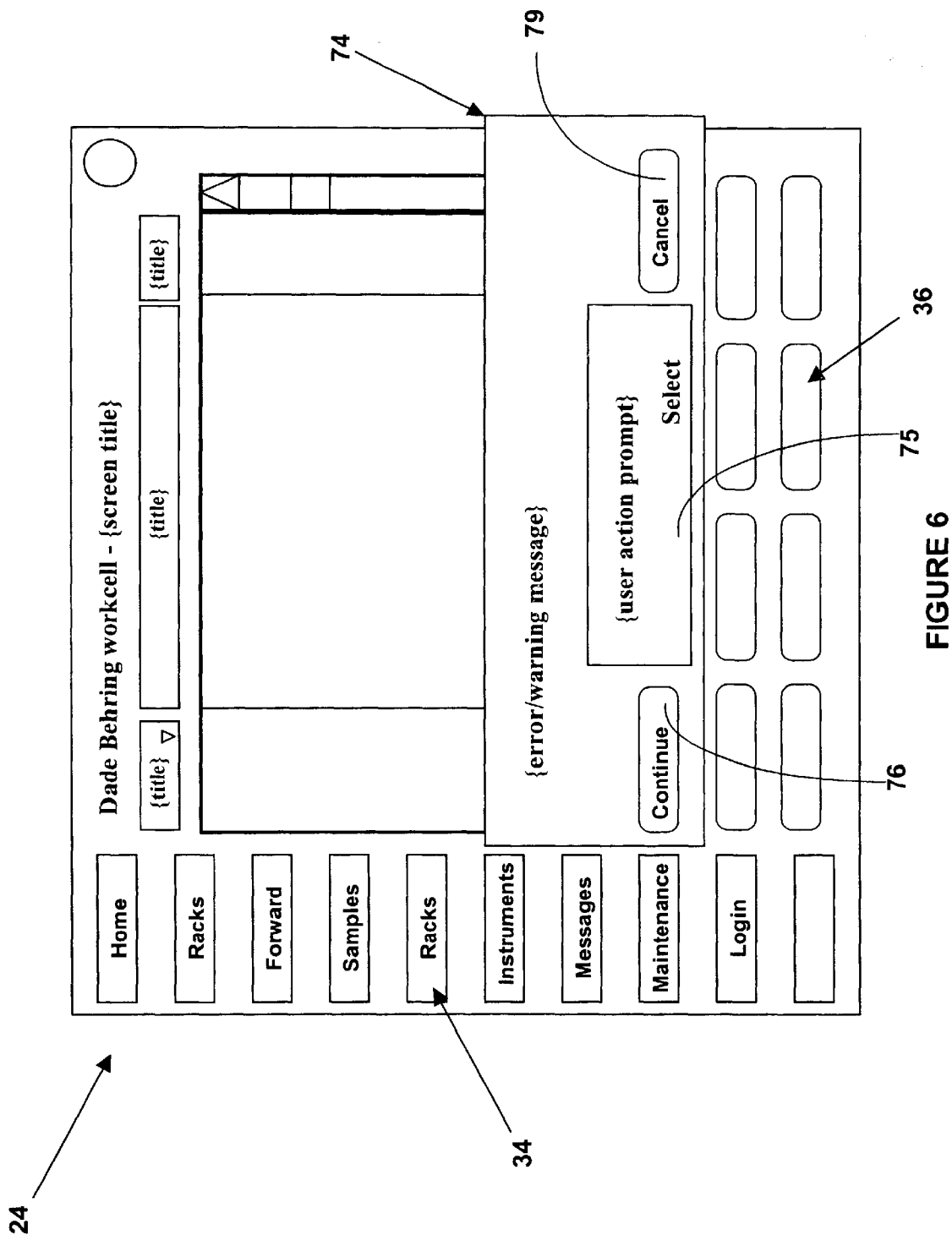
FIG. 6 is a typical respresentation of the computer interface module information display screen of FIG. 2 further illustrating an Error Warning message exemplary of the present invention.

As seen in FIG. 6, if a technician or other user takes an action that warrants an error or warning condition to occur, an error/warning popup window 74 will appear in CIM 24 to alert the user of the condition. The message in the popup window 74 must describe the error or warning and present the means to achieve two possible outcomes. First the ability to proceed despite the condition and second to cancel the action that led to the condition. Generally user should be instructed in a user prompt section 75 in the popup message to press one of two buttons contained within popup window 74, either a Continue button 76 to proceed or a Cancel button 79 to cancel the action. The popup window remains until the issue is resolved (i.e. until button 76 or button 78 is pressed).

Figure 7:
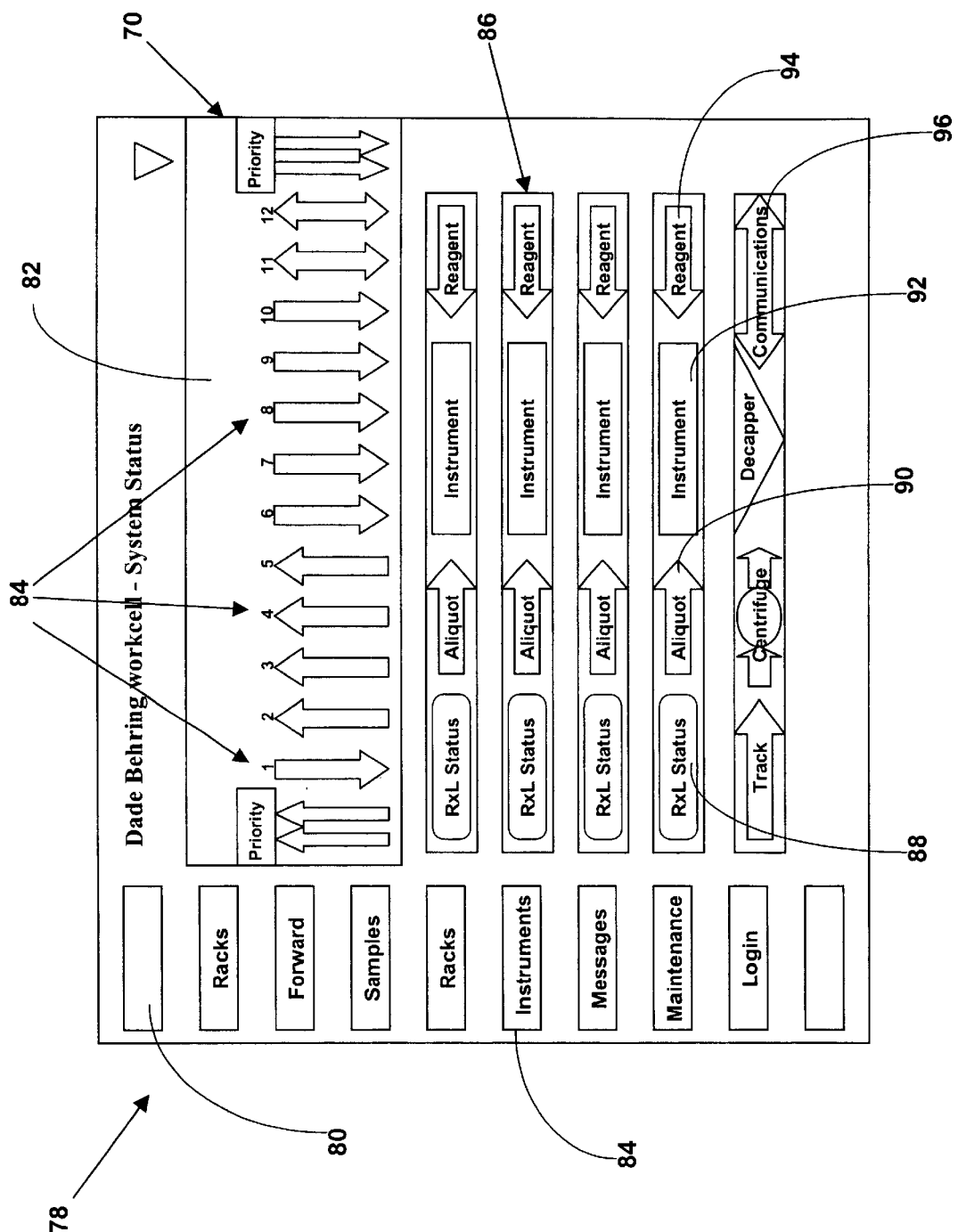
FIG. 7 is a typical representation of the computer interface module information display screen of FIG. 2 further illustrating a view of system operational status exemplary of the present invention

FIG. 7 shows the Home display screen 78 of CIM 24. It is primarily an icon only screen view to present a summary view of overall clinical analytical system 10 operating status. It is the default screen for the system to and can be reached from any other screen on the system by pressing the Home button 80. he Home display screen 78 includes a Input/Output Status panel 82 that shows the status of each sample tube rack 20 in the sample transfer means 16. Each rack icon 84 depicted by an arrow, is also a function button. Pressing the rack icon 84 yields a Rack Details screen described hereinafter for the associated rack position. Priority racks (i.e. Stat Input and Problem Output) will be displayed in pairs on the Rack Details screen.

Up arrow indicate a position being used as an input rack and down arrows indicates use as an output. In general a rack in an I/O position can be empty (white/black outline), waiting (gray/black outline), released (green/black outline), active (yellow/black outline) or a problem (red/black outline). Additionally, a rack position can be either full (indicating its rack status) or empty (double ended arrow—white/white outline). If a rack is dedicated to a specific I/O function the bottom of the arrow will be annotated appropriately to indicate the dedicated function (i.e. S=sorted, I=input only & O=output only).

There are separate analyzer status rows 86 (four are shown in FIG. 7) for each analyzer 12 in the clinical analytical system 10. Each element of the clinical analytical system 10 should be color coded (red/yellow green) to depict its status as described below The Analyzer status icon/button 88 indicates the overall status of the Analyzer 12 and should reflect the color coding of its three main components as described by Aliquot. Pressing the Analyzer status icon/button 88 displays the associated Instrument Details screen with "All" as the default screen specific function button pressed.

Aliquot

The Aliquot icon/button 90 indicates the status of the sample transfer system 16 associated with analyzer 12. It is yellow if the transfer system 16 is getting low on consumables (tips, aliquot wells, tip waste space, etc . . . ), red if in error state or out of consumables, green for all other conditions.

Pressing the aliquot icon/button 90 displays the associated Instrument Details screen with "Aliquot" as the default screen specific function button pressed.

Instrument

The Instrument icon/button 92 indicates the status of the Analyzer 12. It is yellow one of its analysis sub-modules is unavailable (i.e. IMT, HM, etc . . . ), red if in error state, green for all other conditions. Press the Instrument icon/button 92 displays the associated Instrument Details screen with "Instrument" as the default screen specific function button pressed.

Reagent

The Reagent icon/button 94 indicates the status of the reagent inventory on the analyzer 12. It is yellow if getting low on reagent, red if out of any reagent, green for all other conditions. Pressing the Reagent icon/button 94 displays the associated Analyzer 12 Details screen with "Reagent" as the default screen specific function button pressed.

The Clinical Analyzer Component Status panel 96 is similar in performance to the Analyzer 12 status panel. It indicates the status of the various components and/or component groups the sample preparation device 14 and 18 as may be required for the different sample preparation operations such as decapping of a closed sample tube, aliquotting of portions of samples from a primary tube to a secondary tube, sample identification, dilution, centrifugation, etc, in order to prepare the original biological sample for analysis by analyzer 12.

Figure 8:
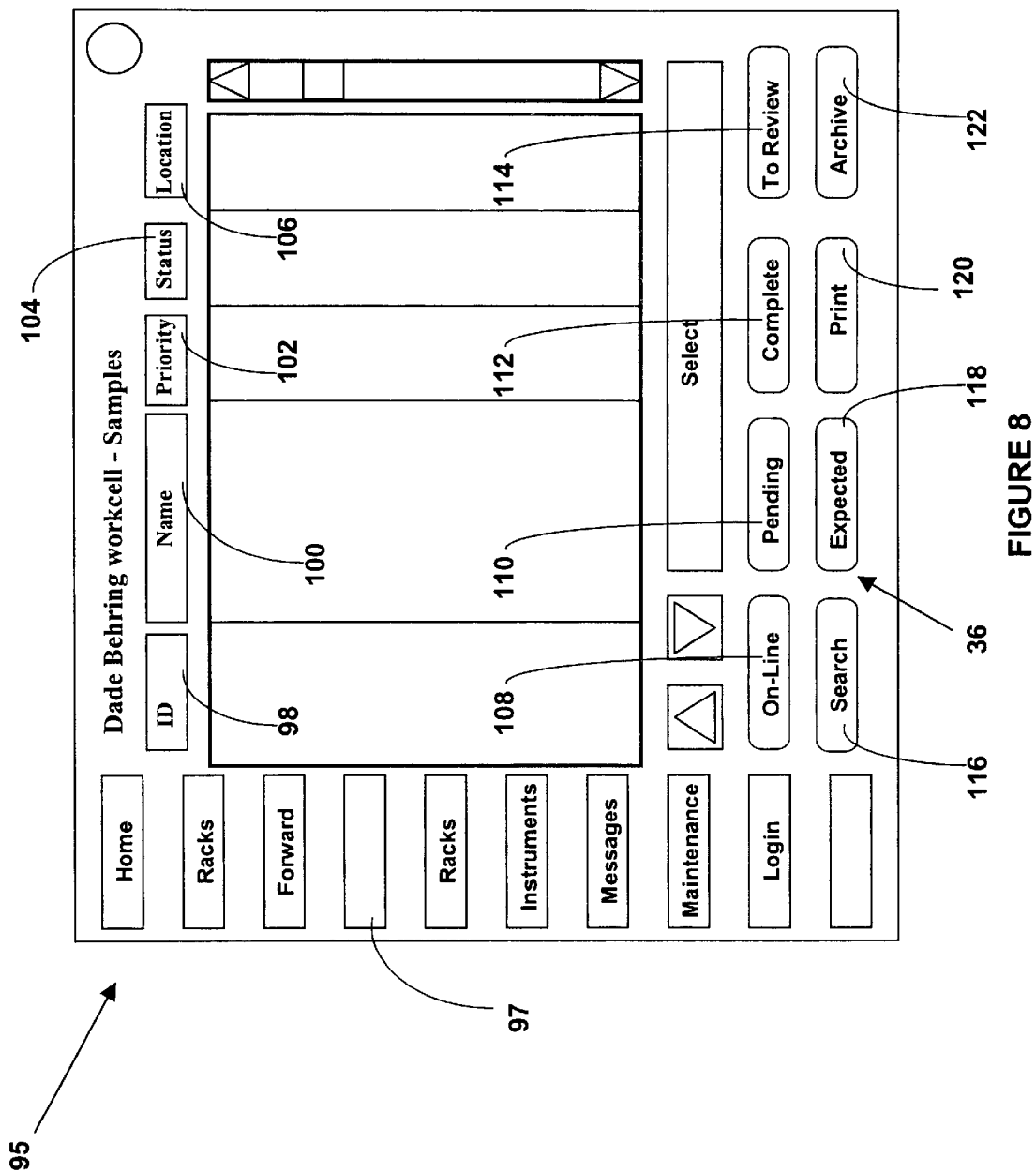
FIG. 8 is a typical representation of the computer interface module information display screen of FIG. 2 further illustrating a list of samples exemplary of the present invention.

FIG. 8 illustrates a Samples screen 95 that may be accessed by touching Sample icon 97 to display a list of samples based on the group selected by the screen function specific buttons 36. ID field 98 displays the Sample ID read by an input barcode reader that is typically integral with either or both of the sample preparation device 14 or analyzer 20. When sorted, ascending order is alphabetical order.

Name field 100 displays the Patient Name as transmitted by the LIS. When sorted, ascending order is alphabetical order. Priority field 102 displays the priority of the sample. When sorted, descending order is:
1. PS Priority Input with (S)tat LIS priority
2. S (S)tat LIS priority
3. PA Priority Input with (A)sap LIS priority
4. A (A)sap LIS priority
5. PR Priority Input with (R)outine LIS priority
6. R (R)outline LIS priority
7. U (U)nknown priority Status field 104 displays the processing status of the sample. When sorted, ascending order is:
1. U Unknown Status
2. P Pre-analytical processing in progress
3. I Instrument(s) processing in progress
4. C Testing complete
5. R Test results sent to LIS Location field 106 identifies the current location of the sample. When sorted, ascending order is:
1. PIn-nn Priority Input rack "n" (where n can have a range of 01 to 02)—position "nn" (where nn can have a range of 01 to 12)
2. POn-nn Priority Output rack "n" (where n can have a range of 03 to 04)—position "nn" (here nn can have a range of 01 to 12)
3. CI-Rnn-nn Centrifuge Input—Rack "nn" (where nn can have a range of 01 to 12)—position "nn" (where nn can have a range of 01 to 32)
4. CR-Rnn-nn Centrifuge Run—Rack "nn" (where nn can have a range of 01 to 12) —position "nn" (where nn can have a range of 01 to 32)
5. CO-Rnn-nn Centrifuge Output—Rack "nn" (where nn can have a range of 01 to 12)—position "nn" (where nn can have a range of 01 to 32)
6. In Instrument buffer n (where n can have a range of 1 to 9)/
7. T Track
8. nn-Rnnn-ann I/O module rack "nn " (where nn can have a range of 01 to 12)—Rack number "nnn" (where nnn can have a range of 100 to 999)—position column "a" (where a can have a range of A to D) row "nn" (where nn can have a range of 01 to 12)
9. Rnnn-ann Rack number "nnn" (where nnn can have a range of 100 to 999)—position column "a" (where a can have a range of A to D) row "nn" (where nn can have a range of 01 to 12)

The On-line the button 108 is activated to display the list of all samples physically on the system. The default sort order is by descending priority (i.e. Stat at the top).

The Pending button 110 is activated to display the list of all with test results pending (i.e. have been delivered to analyzer 12, but results not received). The default sort order is by descending Priority (i.e. Stat at the top).

The Complete button 112 is activated to display the list of all samples completed on a given day. The default sort order is by descending Priority (i.e. Stat at the top).

The Review button 114 is activated to display the list of all samples completed in a given day, but have not had results sent to the LIS. The default sort order is by descending Priority (i.e. Stat at the top).

The Search button 116 activates a popup keyboard to allow the user to enter the search criteria (i.e. Sample ID or Patient Name). After the search criteria has been entered the list of samples includes all samples matching the search criteria. If the search button was already active the results of the current search will be appended to the list (i.e. a series of searches will build a list with the results of all searches). The default sort order is by descending Priority (i.e. Stat at the top).

The Expected button 118 is activated to display the list of all samples that have LIS information, but have not been identified at the system (i.e. may not have been delivered or are in an input rack waiting for processing). The default sort order is by descending Priority (i.e. Stat at the top).

The Print button 120 will cause a printout of the list of Sample ID and Location pairs consistent with the current sample list (i.e. ordered as on the display).

The Archive button 122 activates a popup keypad to allow the user to enter the Archive Day desired. After the archive day has been entered the list of samples includes all samples processed by the system on he day in question. The default sort order is by ascending Sample ID.

Figure 9:
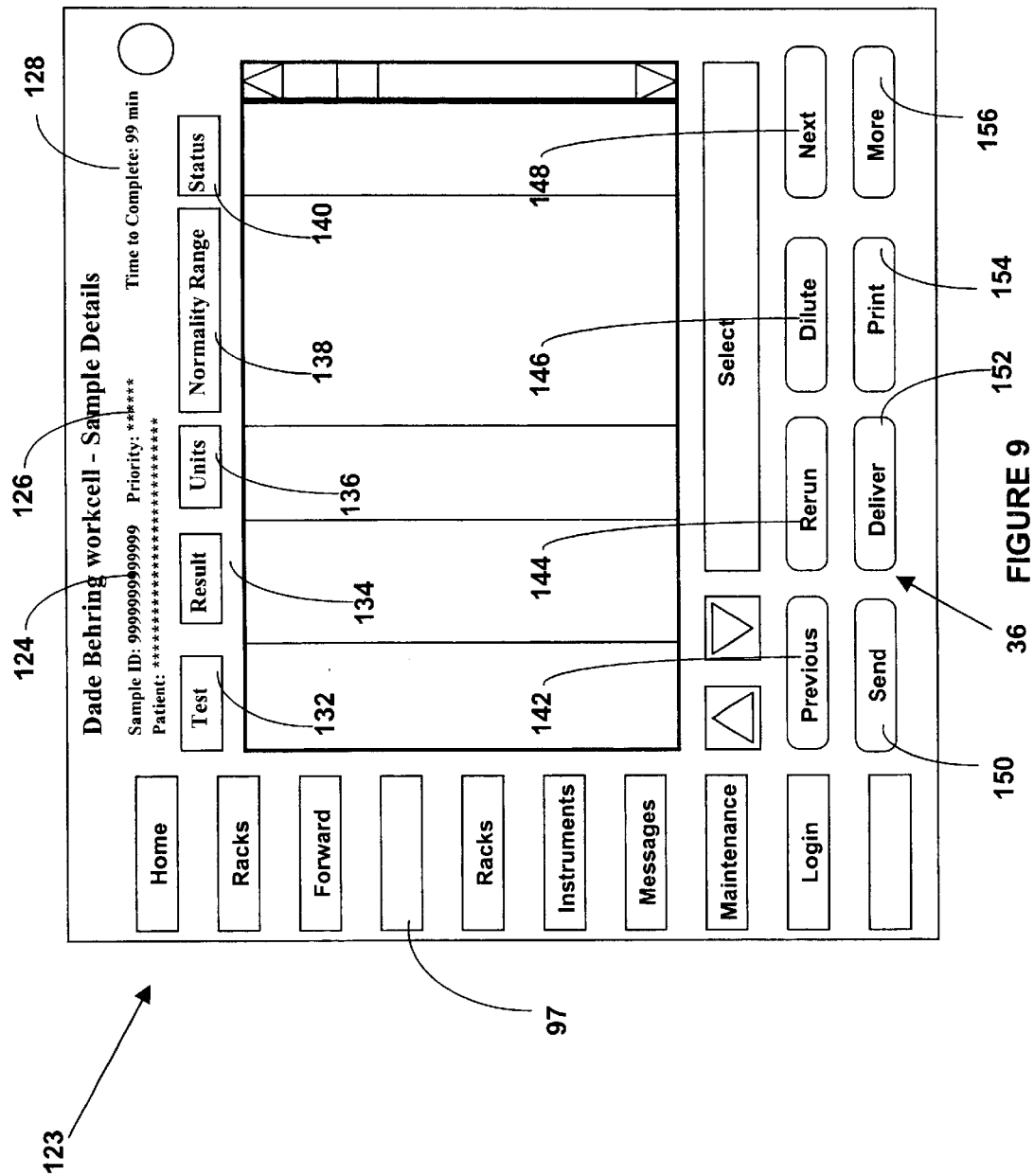
FIG. 9 is a typical representation of the computer interface module information display screen of FIG. 8 illustrating additional detailed information about samples exemplary of the present invention.

FIG. 9 shows a Sample Details screen 123 adapted within CIM 24 to display information on a specific sample. The default sort order is by ascending Test (i.e. Test alphabetical order). A Sample ID field 124 displays the Sample ID read by the barcode reader. When sorted, ascending order is alphabetical order.

A Priority field 126 displays the Priority as transmitted by the LIS.

A Time to complete field 128 displays the estimated time in minutes for all tests ordered for the sample to be complete. If the sample requires pre-analytical processing the time estimate includes the pre-analytical processing time. If all tests have been reported by the instruments this value would be zero.

A Patient field 130 displays the Patient Name as transmitted by the LIS.

A Test field 132 displays the test abbreviation for the ordered tests.

A Result field 134 displays the test result reported by the analyzer 12. If no result has been reported or if the result is suppressed due to a processing error it is blank.

A Unit field 136 displays the unit of measure used in reporting the results.

A Normality Range field 138 displays the high and low result values that are considered normal for this test.

A Status field 140 displays the status of the test ordered for this sample. When sorted, ascending order is:
1. n/a this test is to be performed by an analyzer 12 outside this workcell.
2. "blank" sample for this test has not been delivered to the analyzer 12.
3. Pending sample for this test has been delivered to the analyzer 12 but the analyzer 12 has not completed the test.
4. held analyzer 12 processing complete for this test, results have not been sent to the LIS.
5. error analyzer 12 had an error on this test, results have not been sent to the LIS.
6. sent result for this test has been sent to the LIS.

In the instance that the Sample Details Screen is being displayed on the CIM 24, screen function specific buttons 36 automatically are displayed as a new series of buttons adapted to provide additional flexibility and simplicity in controlling the operation of analyzer 12.

Pressing a button identified as Previous 142 will display the Sample Details for the previous sample in the current list of samples (i.e. if coming from a Samples screen, the sample above this sample on the list; coming from a Racks screen, the sample above this sample on that list.) as currently ordered on the originating screen.

Pressing a button identified as Rerun 144 will schedule the highlighted test to be rerun. If the highlighted test was already scheduled for rerun, the rerun request is canceled. To execute the rerun request Send must be pressed.

Pressing button identified as Dilute 146 will schedule the highlighted test to be rerun with a dilution. A numeric keyboard will popup to allow a dilution factor to be entered. If the highlighted test was already scheduled for rerun with a dilution, the rerun with dilution request is canceled. To execute the rerun with dilute request Send must be pressed.

Pressing button identified as Next 148 will display the Sample Details for the next sample in the current list of samples (i.e. if coming from a Samples screen, the sample above this sample on the list; if coming from a Racks screen, the sample above this sample on that list.) as currently ordered on the originating screen.

Pressing button identified as Send 150 will cause the system to send any unsent sample test results to the LIS. Any tests with rerun requested will not be sent to the LIS. Pressing Send also activates all rerun requests. If the screen is exited with unsent rerun requests a popup error window will appear to alert the user. Exiting without sending rerun requests cancels all reruns.

Pressing a button identified as Deliver 152 will cause the sample to be delivered to the Problem Output lane the in the I/O Module if the sample is in the system. Otherwise an error message will be displayed to indicate the sample cannot be delivered.

Pressing a button identified as Print 154 causes the current sample results to be printed.

Figure 10:
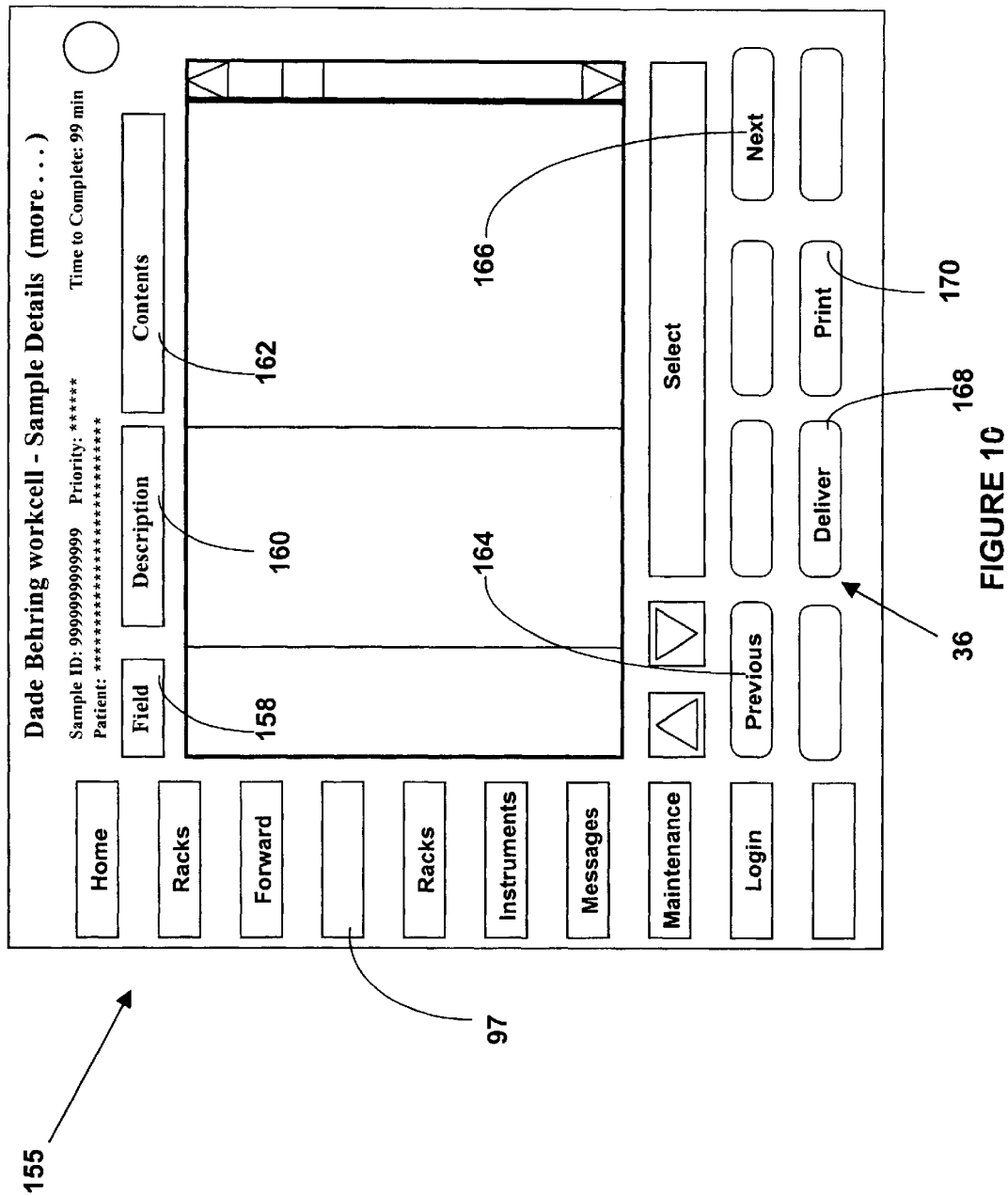
FIG. 10 is a typical representation of the computer interface module information display screen of FIG. 2 further illustrating laboratory information data about samples exemplary of the present invention.

Pressing a button identified as More 156 will cause another screen as illustrated in FIG. 10 and identified as Sample Details (more . . . ) screen 155 to appear and display additional details for the current sample by giving access to the entire LIS data record. The default sort order is by Field number.

Pressing a button identified as Field 158 displays the field number of the LIS Patient, Order and/or Result record. When sorted, ascending order is:
1. Pnn Patient record field "nn" (where nn can have a range of 01 to 35)
2. Onn Order record field "nn" (where nn can have a range of 01 to 31)
3. Rnn Result record field "nn" (where nn can have a range of 01 to 14)

Pressing a button identified as Description 160 displays a brief description of the LIS record component. When sorted, ascending order is alphabetical order.

Pressing a button identified as Contents 162 displays the contents of the LIS record component as transmitted or as assembled for transmission. When sorted, ascending order is numerical order followed by alphabetical order.

Pressing a button identified as Previous 164 displays the Sample Details for the previous sample in the current list of samples (i.e. if coming from a Samples screen, the sample above this sample on the list; if coming from a Racks screen, the sample above this sample on that list.) as currently ordered on the originating screen.

Pressing a button identified as Next 166 display the Sample Details for the next sample in the current list of samples (i.e. if coming from a Samples screen, the sample above this sample on the list; if coming from a Racks screen, the sample above this sample on that list.) as currently ordered on the originating screen.

Pressing a button identified as Deliver 168 causes the sample to be delivered to the Problem Output lane in the I/O Module if the sample is in the system. Otherwise an error message will be displayed to indicate the sample cannot be delivered.

Pressing a button identified as Print 170 causes the current sample results to be printed.

Figure 11:
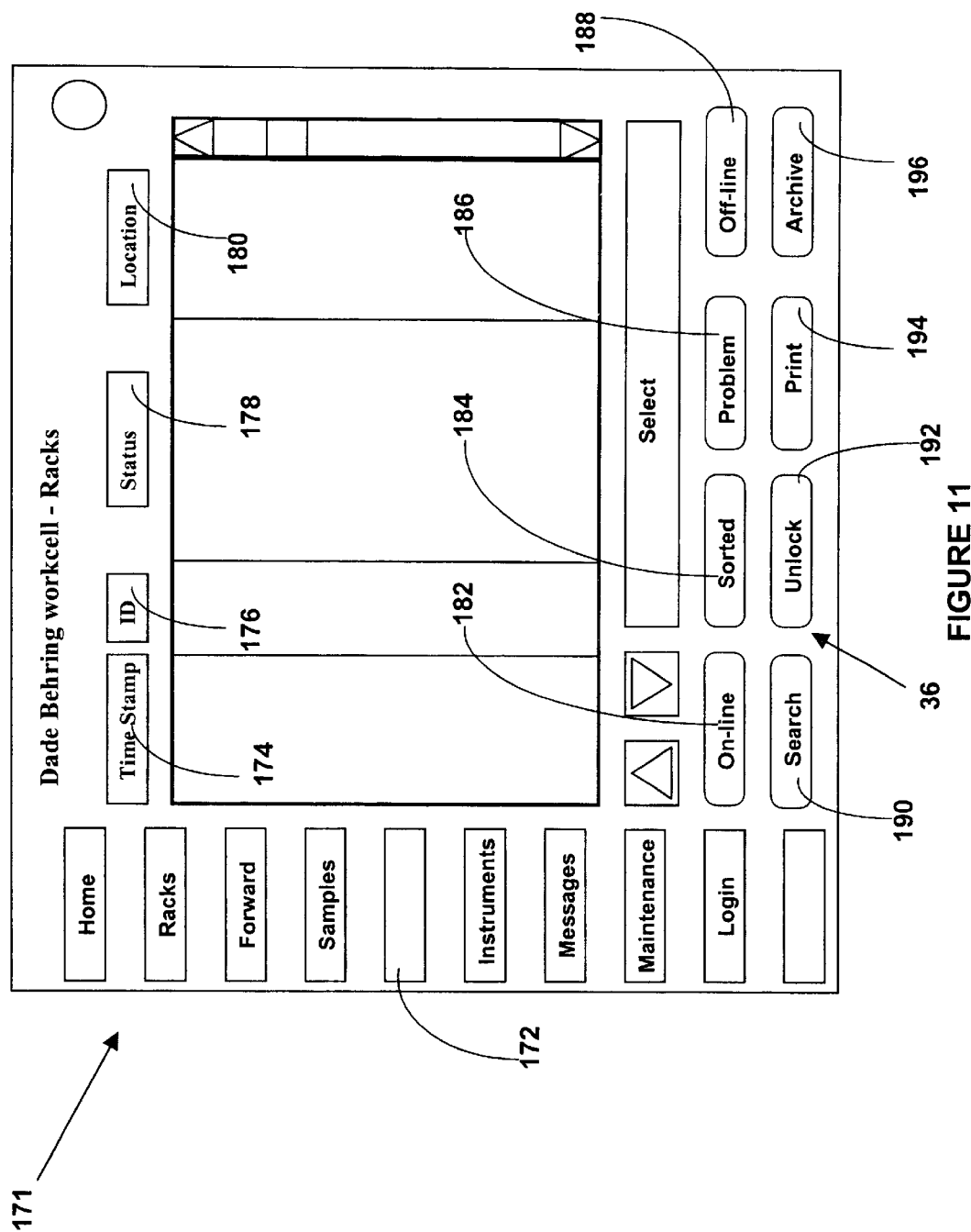
FIG. 11 is a typical representation of the computer interface module information display screen of FIG. 2 further illustrating information about sample racks exemplary of the present invention.

FIG. 11 shows a Racks screen 171 adapted within CIM 24 to display additional information on a specific sample that may be readily accessed by selecting the Racks button 172 from among the group of function buttons 34. The Racks screen displays a list of racks based on the group selected by the screen specific function buttons 36. The default rack group is On-line.

Pressing a button identified as Timestamp 174 displays the time and date (mm-dd hh:mm) when this rack information was last changed. When sorted, descending order is from now to the past (the appropriate year, "yyyy", is assumed to prefix the displayed timestamp for sorting purposes).

Pressing a button identified as ID 176 displays the Rack number "Rnnn" (where nnn can have a range of 100 to 999).

Pressing a button identified as Status 178 displays the status of the sample rack. When sorted, ascending order is:
1. Empty The rack is known to be empty.
2. Unknown The rack status is unknown.
3. Input-Queued This rack has been identified as an input rack and is waiting for unloading.
4. Input-Active This is the input rack that is currently being unloaded by the I/O module.
5. Output-Empty This rack has been identified as an output rack and is empty waiting for loading.
6. Output-Active This is the output rack that is currently being loaded by the I/O module.
7. Output-Pending This rack contains some sample(s) that do not have all the test result for tests ordered on this clinical analytical system 10 reported.
8. Output-Ready All samples in the rack have completed the tests ordered for this workcell.
9. Output-Off-line This rack was last used as an output rack and is no longer on the system.
10. Sorted-Empty This rack has been identified as a sorted output rack and is currently empty waiting for sample tubes to be loaded.
11. Sorted-Active This is the sorted output rack that is currently being loaded by the I/O module.
12. Sorted-Pending This rack only contains samples that require further processing outside the clinical analytical system 10 but also contains some sample(s) that do not have all the test results for tests ordered on this clinical analytical system 10 reported.
13. Sorted-Ready This rack only contains samples that require further processing outside the workcell. All samples in the rack have completed the tests ordered for this workcell.
14. Sorted-Off-line This rack was last used as a sorted output rack and is no longer on the system.

Pressing a button identified as Location 180 displays the location of the sample rack within the clinical analytical system 10. When sorted, ascending order is:
1. PI-n Priority Input location "n" (where n can have the range of 1 to 2).
2. S-nn I/O module Slot "nn" (where nn can have the range of 1 to 12).
3. PO-n Priority Output location "n" (where n can have the range of 1 to 2).
4. ?-nn Rack has been removed from the workcell. Last location on system was I/O module slot "nn" (where nn can have the range of 1 to 12).

FIG. 11 further shows a series of buttons within the Racks screen adapted within CIM 24 to display additional information on a specific sample that may be readily accessed by selecting one of eight additional rack information buttons from among the group of function specific buttons 36. These eight additional rack information buttons readily and simply provide information about all racks within the clinical analytical system 10.

Pressing a button identified as On-line 182 causes the list of racks to include all racks physically on the system. The default sort order is by ascending Location.

Pressing a button identified as Sorted 184 causes list of racks to include all racks that were used for sorted output today. The default sort order is by descending Timestamp (i.e. most recent information at the top).

Pressing a button identified as Problem 186 causes the list of racks to include the problem output racks on the system. The default sort order is by ascending Location.

Pressing a button identified as Off-line 188 causes the list of racks to include all racks that were removed from the system today. The default sort order is by descending Timestamp (i.e. most recent information at the top).

Pressing a button identified as Search 190 causes will activate a popup keyboard (not shown) to allow the user to enter the search criteria (i.e. Rack ID). After the search criteria has been entered the list of racks includes all racks matching the search criteria. If the search button was already active the results of the current search will be appended to the list (i.e. a series of searches will build a list with the results of all searches). The default sort order is by descending timestamp (i.e. most recent information at the top).

Pressing a button identified as Unlock 192 causes will unlock the highlighted rack.

Pressing a button identified as Print 194 causes a printout of the list of Rack ID, Status and Location consisted with the current rack list (i.e. ordered as on the display).

Pressing a button identified as Archive 196 causes the list of racks to include all racks that were removed from the system. The default sort order is by descending Timestamp (i.e. most recent information at the top).

Figure 12:
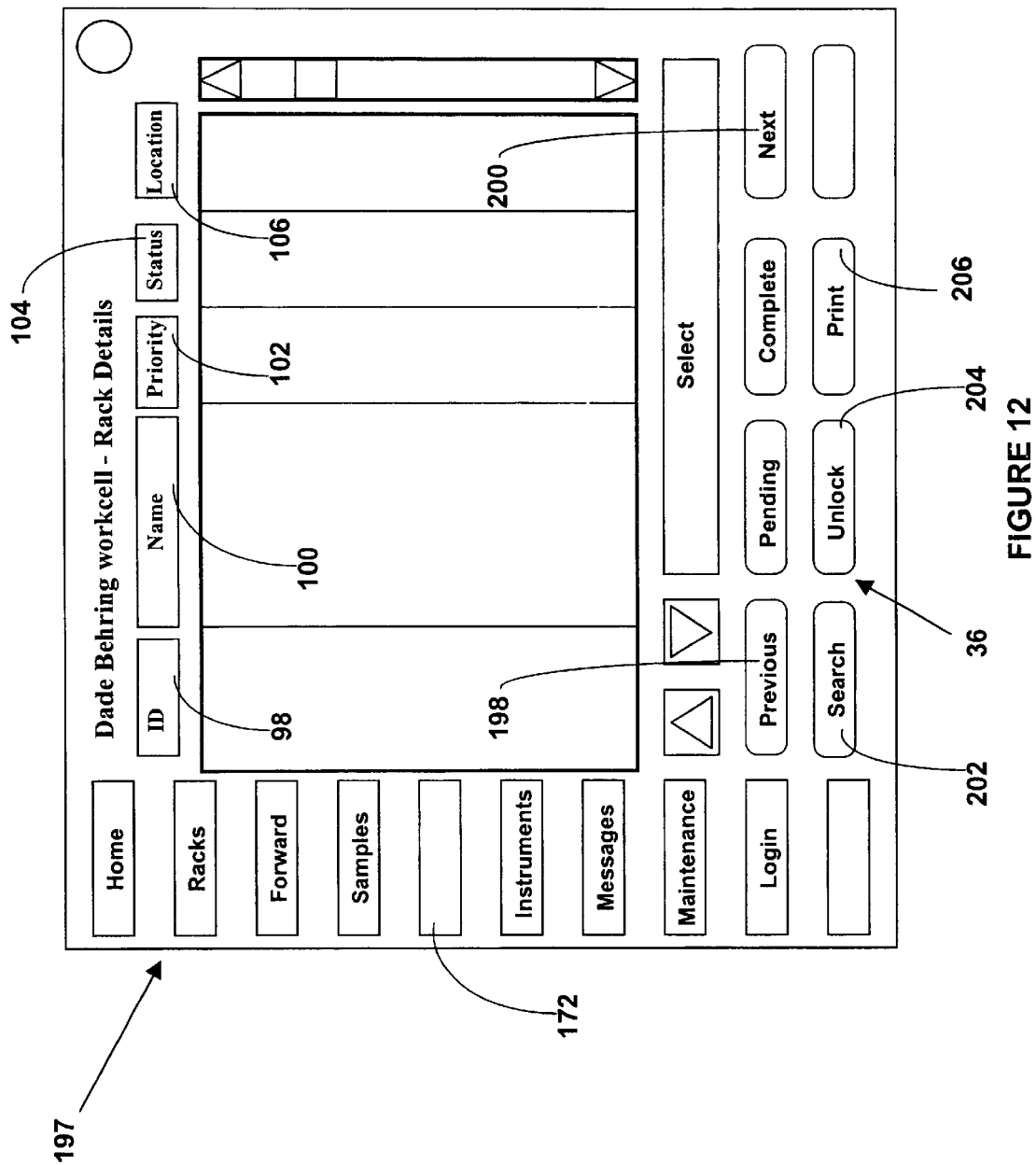
FIG. 12 is a typical representation of the computer interface module information display screen of FIG. 11 illustrating additional detailed information about sample racks exemplary of the present invention.

FIG. 12 shows a Rack Details screen 197 adapted within CIM 24 to display additional information on a specific rack that may be readily accessed by activating the Select button 60 when the rack of interest is highlighted. The default sort order for this screen is by ascending Location (i.e. Rack Map order).

Several fields are the same as illustrated in FIG. 8 including Sample ID 98, Patient Name 100, Priority 102, Status 104, and Location 106.

Pressing a button identified as Previous 198 will display the Rack Details for the previous rack in the current, list of racks as currently ordered on the originating screen.

Pressing a button identified as Next 200 will display the Rack Details for the next rack in the current list of racks as currently ordered on the originating screen.

Pressing a button identified as Search 202 will activate a popup keyboard to allow the user to enter the criteria (i.e. Rack ID). After the search criteria has been entered the Rack Details screen will be displayed for the entered Rack ID.

Pressing a button identified as Unlock 204 will unlock the rack.

Pressing a button identified as Print 206 will cause the Rack Map to be printed (i.e. Rack ID followed by Sample ID/Location pairs).

Figure 13:
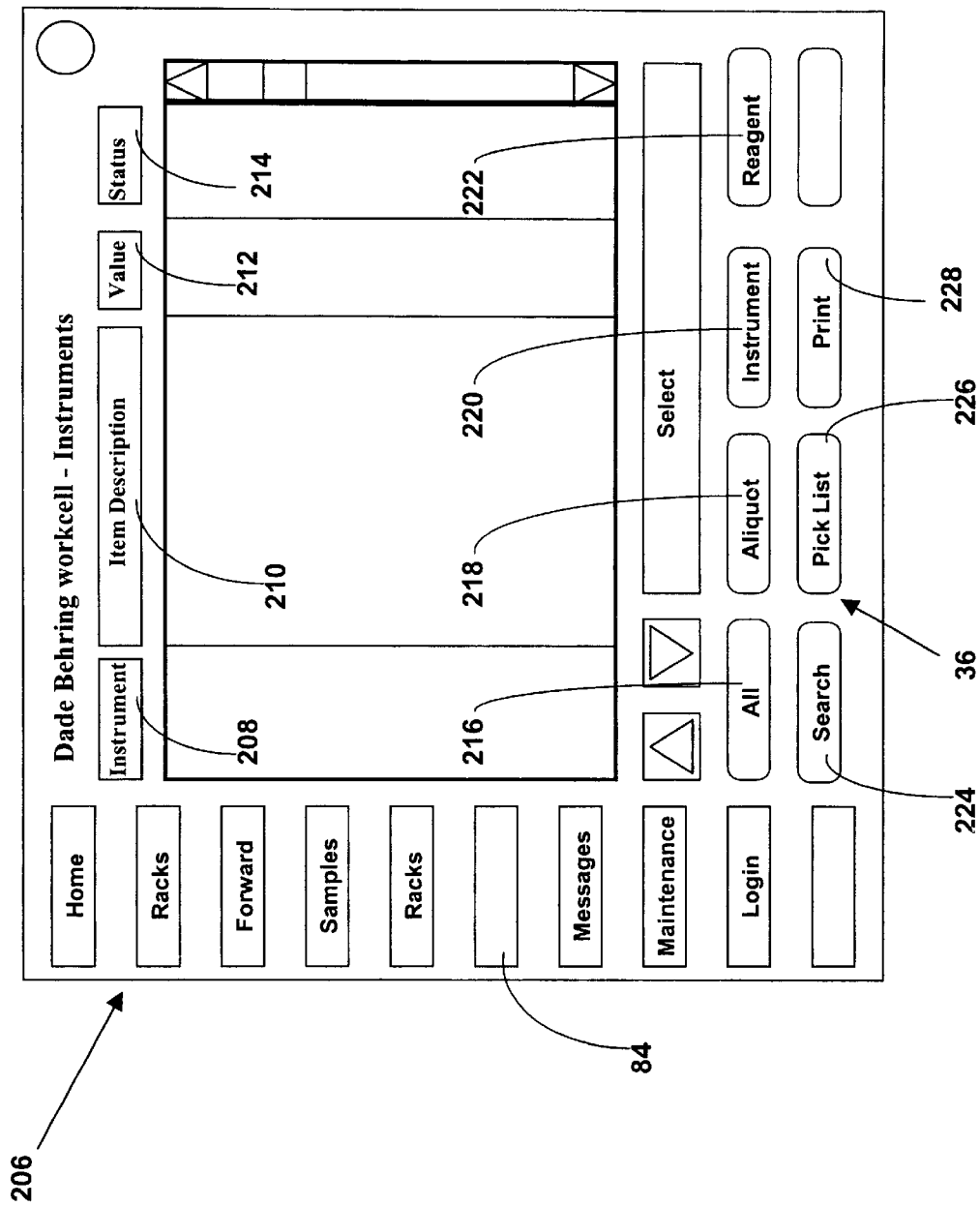
FIG. 13 is a typical representation of the computer interface module information display screen of FIG. 2 further illustrating information about the plurality of automated devices exemplary of the present invention.

FIG. 13 shows an Instruments screen 206 adapted within CIM 24 to display a list of status messages for all instruments in the clinical analytical system 10 that may be readily accessed by selecting the Instruments button 84 from among the group of function buttons 34. The Racks screen displays a list of racks based on the group selected by the screen specific function buttons. The default message group is All.

Pressing a button identified as Instruments 208 displays the Instrument ID, identical to the one as transmitted by the LIS. When sorted, ascending order is alphabetical order.

Pressing a button identified as Item Description 210 displays a description of the item of interest. When sorted, ascending order is alphabetical order.

Pressing a button identified as Value 212 displays the value associated with the item description. When sorted, ascending order is numeric order followed by alphabetical order.

Pressing a button identified as Status 214 displays the status of the item value. When sorted, descending order is.
1. Alarm
2. Error
3. High
4. Low
5. Warning
6. Normal FIG. 13 further shows a series of buttons within the Instruments screen 206 adapted within CIM 24 to display additional information on status messages that may be readily accessed by selecting one of eight additional rack information buttons from among the group of function specific buttons 36. The eight additional status message buttons readily and simply provide information about all within the clinical analytical system 10.

Pressing a button identified as All 216 causes the list of status messages to include all messages for all analyzers. The default sort order is by descending Status (i.e. most critical information at the top).

Pressing a button identified as Aliquot 218 causes the list of status messages to include only messages pertaining to the aliquot portion of all instruments. The default sort order is by descending Status (i.e. most critical information at the top).

Pressing a button identified as Instrument 220 the list of status messages includes only messages pertaining to an analysis portion of all analyzers 12. The default sort order is by descending Status (i.e. most critical information at the top).

Pressing a button identified as Reagent 222 causes the list of status messages to include only messages pertaining to the reagent inventory on all analyzers. The default sort order is by descending Status (i.e. most critical information at the top).

Pressing a button identified as Search 224 will activate a popup keyboard to allow the user to enter the search criteria (i.e. Instrument ID). After the search criteria has been entered the Instrument Details screen will be displayed for the entered Instrument ID.

Pressing a button identified as Pick List 226 causes the list of status messages to include only messages pertaining to low reagent inventory on all analyzers. The default sort order is by ascending Item Description (i.e. reagent alphabetical order).

Pressing a button identified as Print 228 causes the currently displayed messages to print.

Figure 14:
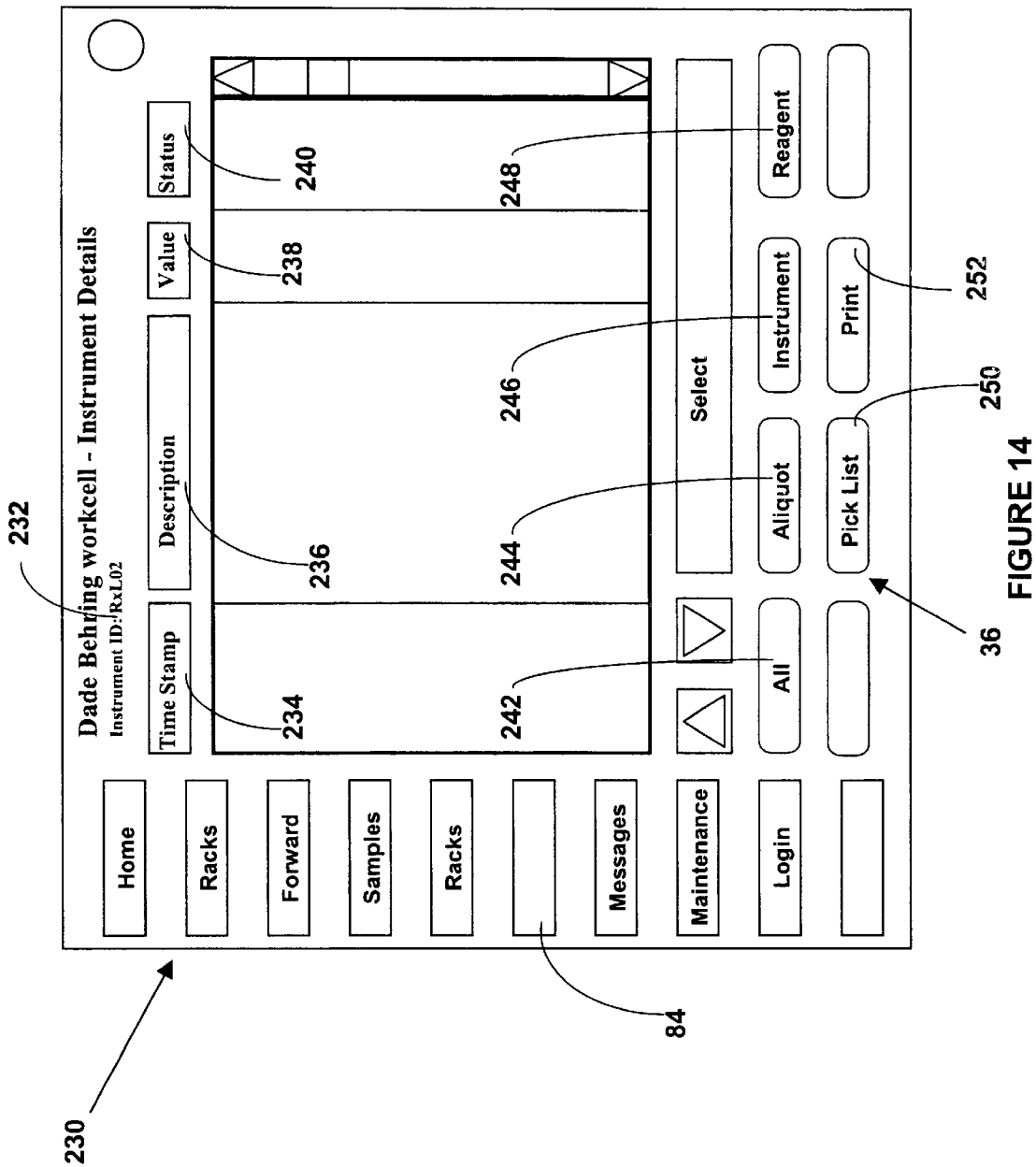
FIG. 14 is a typical representation of the computer interface module information display screen of FIG. 2 further illustrating information contained in general messages exemplary of the present invention.

FIG. 14 show an Instrument Details screen adapted within CIM 24 to display a list of status message associated with a specific analyzer 12 that may be readily accessed by activating the Select button 60 when the analyzer 12 of interest is highlighted. The default message group is All.

Pressing a button identified as Instrument ID 232 displays the Instrument ID, identical to the one as transmitted by the LIS. When sorted, ascending order is alphabetical order.

Pressing a button identified as Timestamp 234 displays the time and date (mm-dd hh:mm) when this analyzer information was last changed. When sorted, descending order is from now to the past (the appropriate year, "yyyy", is assumed to prefix the displayed timestamp for sorting purposes).

Pressing a button identified as Item Description 236 displays a description of the item of interest. When sorted, ascending order is alphabetical order.

Pressing a button identified as Value 238 displays the value associated with the item description. When sorted, ascending order is numeric order followed by alphabetical order.

Pressing a button identified as Status 240 displays the status of the item value. When sorted, descending order is.
1. Alarm
2. Error
3. High
4. Low
5. Warning
6. Normal Pressing a button identified as All 242 causes the list of status messages to include all messages for this analyzer 12. The default sort order is by descending Status (i.e. most critical information at the top).

Pressing a button identified as Aliquot 244 causes the list of status messages to include only messages pertaining to the aliquot portion of this analyzer 12. The default sort order is by descending Status (i.e. most critical information at the top).

Pressing a button identified as Instrument-M 246 the list of status messages includes only messages pertaining to an analysis portion of this analyzer 12. The default sort order is by descending Status (i.e. most critical information at the top).

Pressing a button identified as Reagent 248 causes the list of status messages to include only messages pertaining to the reagent inventory on this analyzer 12. The default sort order is by descending Status (i.e. most critical information at the top).

Pressing a button identified as Pick List 250 causes the list of status messages to include only messages pertaining to low reagent inventory on this analyzer 12. The default sort order is by ascending Item Description (i.e. reagent alphabetical order).

Pressing a button identified as Print 252 causes the currently displayed messages to print.

Figure 15:
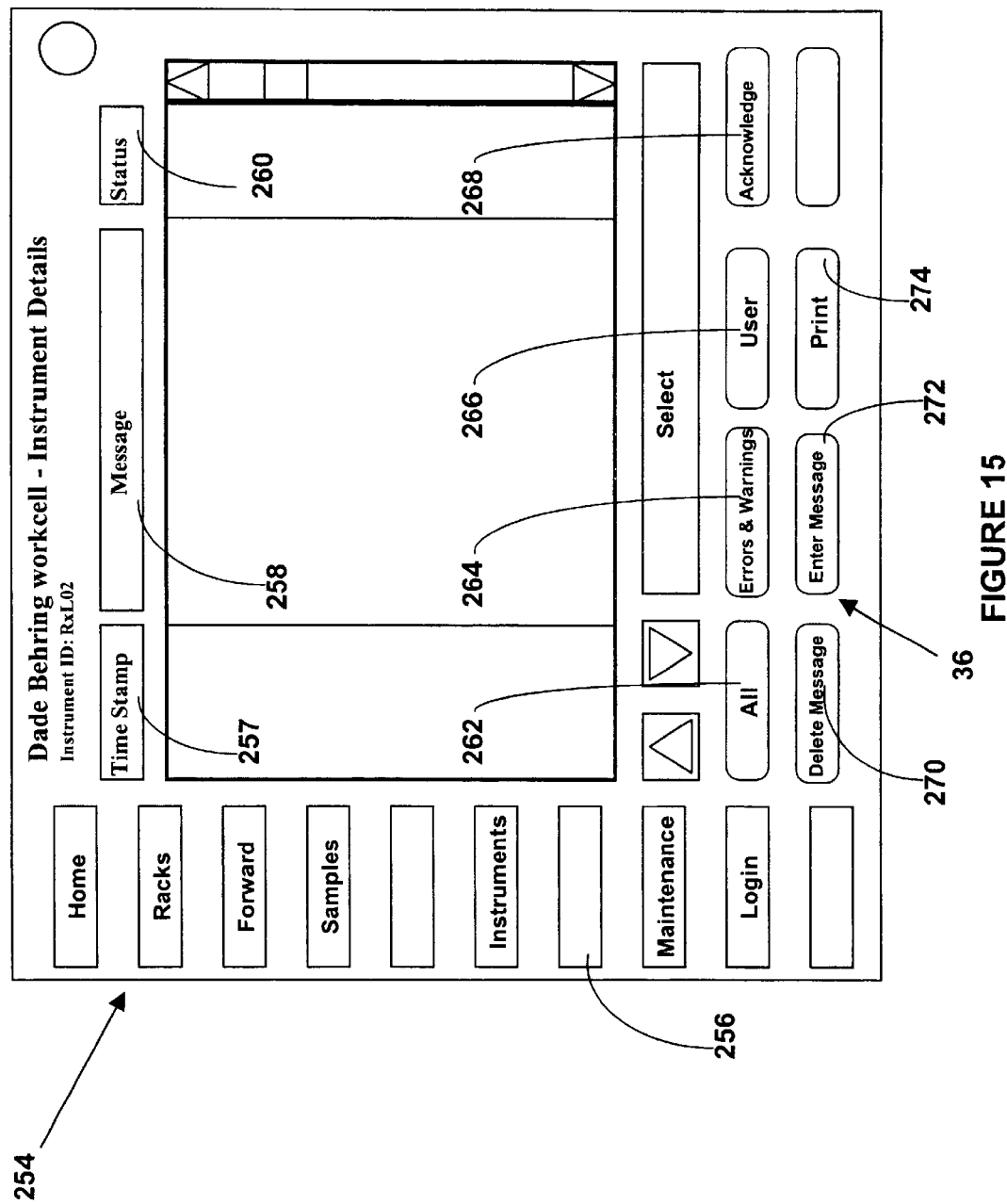
FIG. 15 is a typical representation of the computer interface module information display screen of FIG. 14 providing a list of all general messages exemplary of the present invention.

FIG. 15 shows an Messages screen 254 adapted within CIM 24 to display a list of general messages associated with a specific analyzer 12 that may be readily accessed by selecting the Messages button 256 from among the group of function buttons 34. The default message group is All.

Pressing a button identified as Timestamp 257 displays the time and date (mm-dd hh:mm) when this message was posted. When sorted, descending order is from now to the past (the appropriate year, "yyyy", is assumed to prefix the displayed timestamp for sorting purposes).

Pressing a button identified as Message 258 displays the contents of the message. System originated message will change languages as selected but user entered messages will not.

Pressing a button identified as Status 260 displays the current status of the message. When sorted, descending order is.

1. Alarm Message is indicating an error condition and has an associated audible alarm sounding.
2. Error Message is indicating an error condition.
3. Warning Message is a warning.
4. User Message was entered by a user.
5. Information Message is for information only.
6. Acknowledged Message was acknowledged by user.
7. Deleted Message was deleted by user. Deleted messages will only be displayed on a space available basis or until deleted a second time.

Pressing a button identified as All 262 causes the list of messages to include all messages. The default sort order is by descending status (i.e. most critical information at the top).

Pressing a button identified as Errors & Warnings 264 causes the list of messages to include only error and warning messages. The default sort order is by descending timestamp (i.e. most recent information at the top).

Pressing a button identified as User 266 the list of messages includes only user entered messages. The default sort order is by descending timestamp (i.e. most recent information at the top).

Pressing a button identified as System Set-Up 290 causes a list of System Setup screen selections to be displayed. The default sort order is by ascending description (i.e. alphabetical order).

Pressing a button identified as Chemistry 292 causes a list of Chemistry Setup screen selections Pressing a button identified as Acknowledge 268 acknowledges the highlighted message. The User ID currently logged in is associated with the acknowledgement in the system log. If no user is logged in (i e. User ID is 000) an error message popup window will alert the user.

Pressing a button identified as Delete Message 270 deletes the highlighted message. The User ID currently logged in is associated with the deletion in the system log. If no user is logged in (i.e. User ID is 000) an error message popup window will alert the user.

Pressing a button identified as Enter Message 272 activates a popup keyboard to allow the user to enter a message. The User ID currently logged in is associated with the entered user message in the system log. If no user is logged in (i.e. User ID is 000) an error message popup window will alert he user.

Pressing a button identified as Print 274 causes the currently viewable messages to print.

Figure 16:
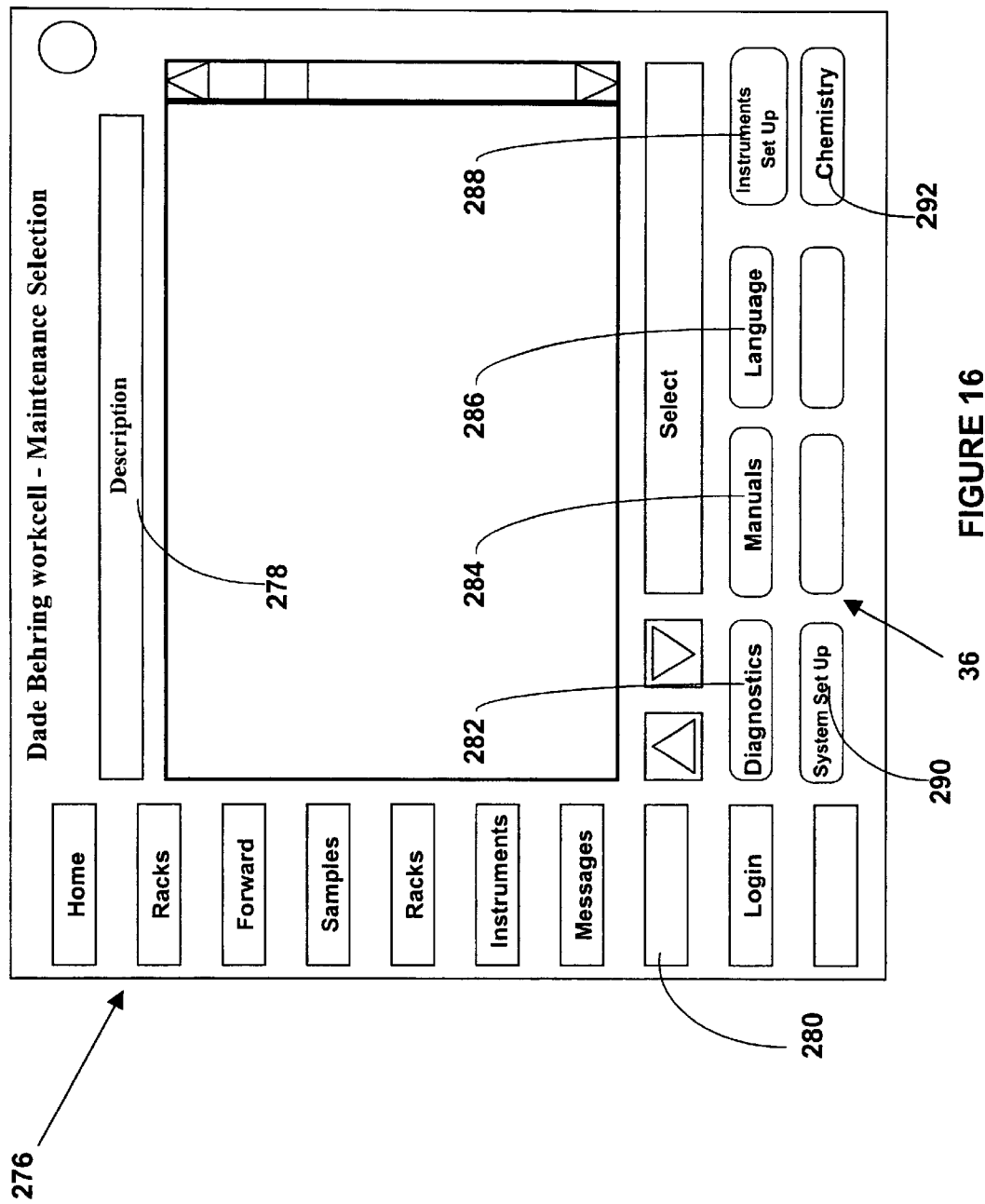
FIG. 16 is a typical representation of the computer interface module information display screen of FIG. 2 further illustrating maintenance selection options exemplary of the present invention.

FIG. 16 shows an Maintenance Selection screen 276 adapted within CIM 24 to display a list of possible maintenance selections associated with a specific analyzer 12 that may be readily accessed by selecting the Maintenance button 280 from among the group of function buttons 34.

The field identified as Description 278 displays a description of the possible maintenance selections based on the function button 34 that is currently active.

Pressing a button identified as Diagnostics 282 causes a list of Diagnostic screen selections to be displayed. The default sort order is by ascending description (i.e. alphabetical order).

Pressing a button identified as Manuals 284 causes a list of Manual screen selections to be displayed. The default sort order is by ascending description (i.e. alphabetical order).

Pressing a button identified as Language 286 causes a list of Language selections to be displayed. The default sort order is by ascending description (i.e. alphabetical order). To change the language selection, it is only necessary to highlight the desired language and press the Language button.

Pressing a button identified as Instruments Setup 288 causes a list of Instrument Setup screen selection to be displayed. The default sort order is by ascending description (i.e. alphabetical order).

Pressing a button identified as System 290 causes a list of System Setup screen selections to be displayed. the default sort order is by ascending description (i.e. alphabetical order).

Pressing a button identified as Chemistry 292 causes a list of Chemistry Setup screen selections to be displayed. The default sort order is by ascending description (i.e. alphabetical order).

Figure 17A:
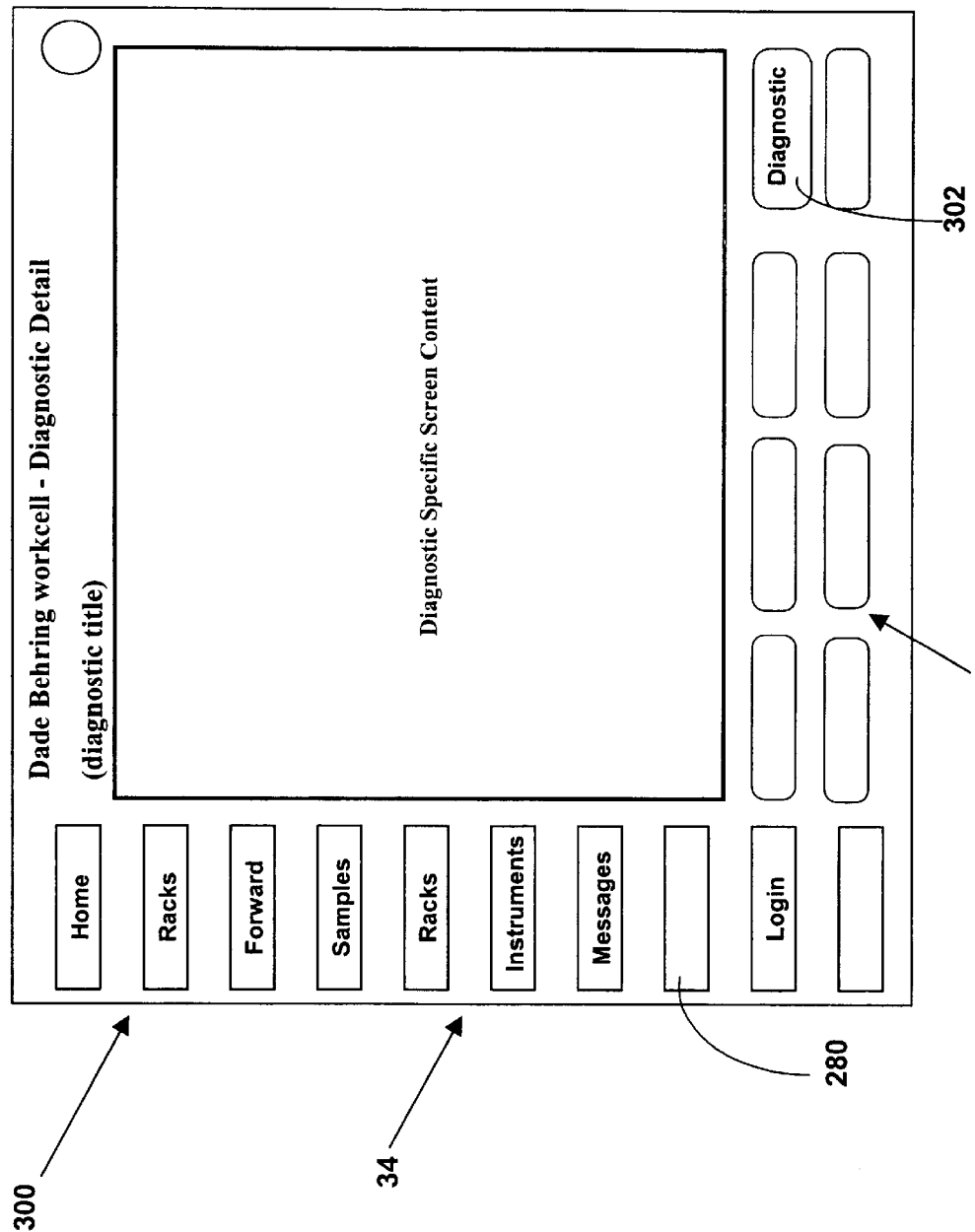
FIG. 17A is a typical representation of the computer interface module information display screen of FIG. 2 further illustrating diagnostic information exemplary of the present invention.

FIG. 17A shows a Diagnostic Selection screen 300 adapted within CIM 24 to display a list of possible diagnostic data associated with a specific analyzer 12 that may be readily accessed by selecting the Diagnostic button 302 from among the group of function specific buttons 36. This screen contains information about the analyzer 12 that is useful in making a operational diagnostic evaluation before or during routine quality control procedures.

Figure 17B:
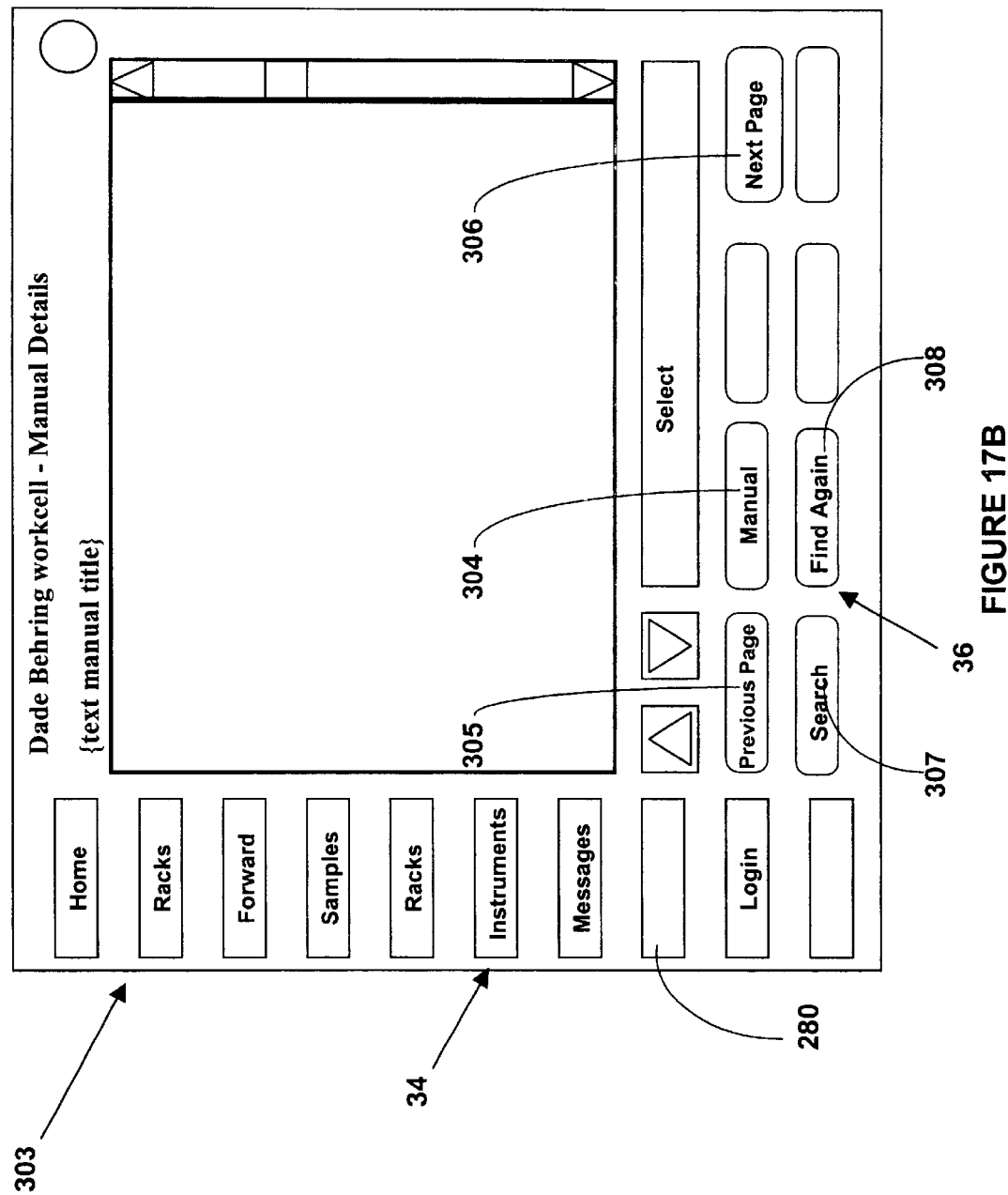
FIG. 17B is a typical representation of the computer interface module information display screen of FIG. 2 further illustrating operating manual information exemplary of the present invention.

FIG. 17B shows a Manual Details screen 303 adapted within CIM 24 to display the operating manual of a specific analyzer 12 or sample preparation device 18 that may be readily accessed by selecting the Manual button 304 from among the group of function specific buttons 36. Touch button 305 accesses the previous page of the operational manual; touch button 306 accesses the previous page of the operational manual; touch button 307 accesses a search function within the operational manual; and, touch button 308 accesses a find again function within a search of the operational manual.

Figure 17C:
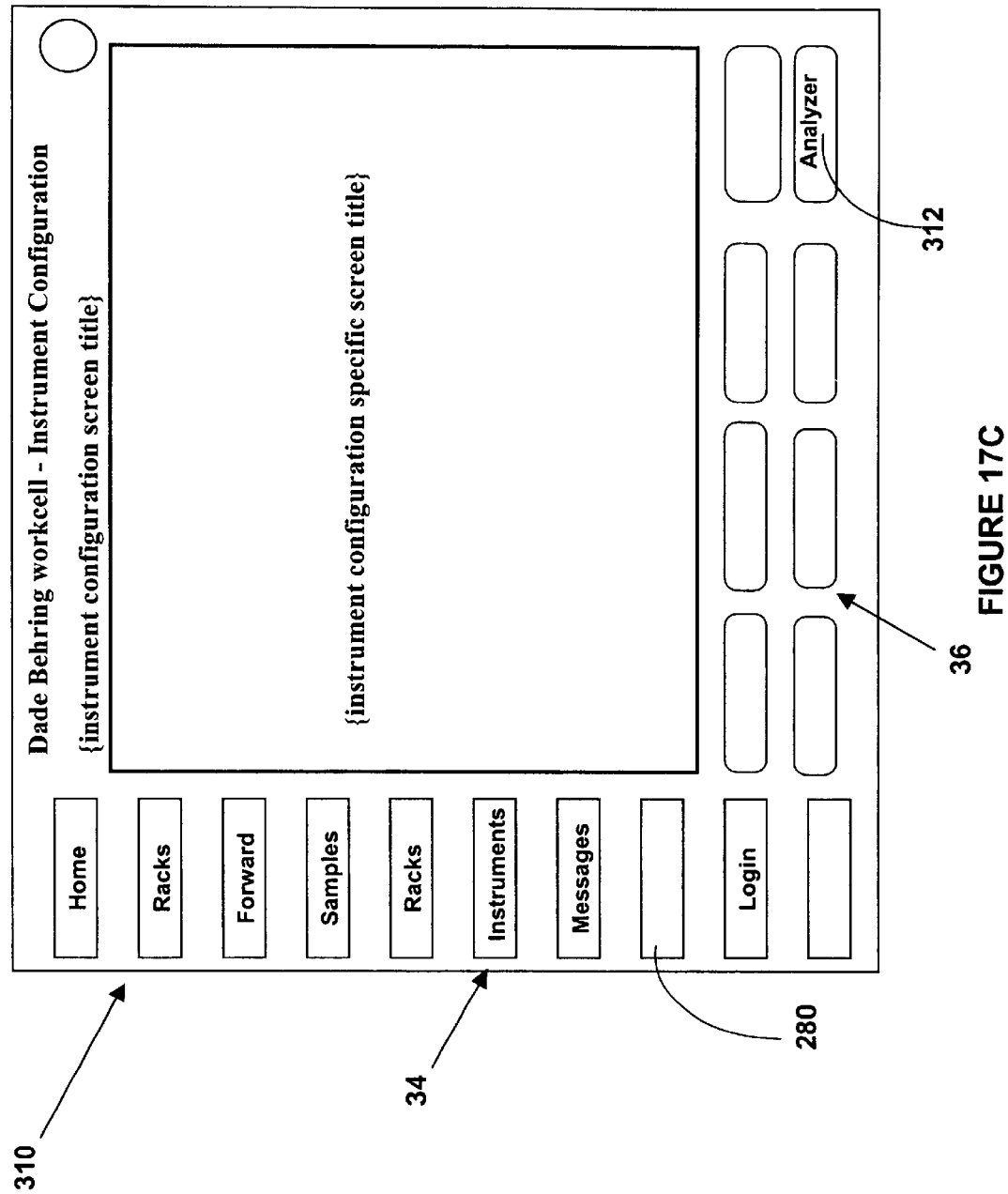
FIG. 17C is a typical representation of the computer interface module information display screen of FIG. 2 further illustrating analyzer configuration information exemplary of the present invention.
Figure 17D:
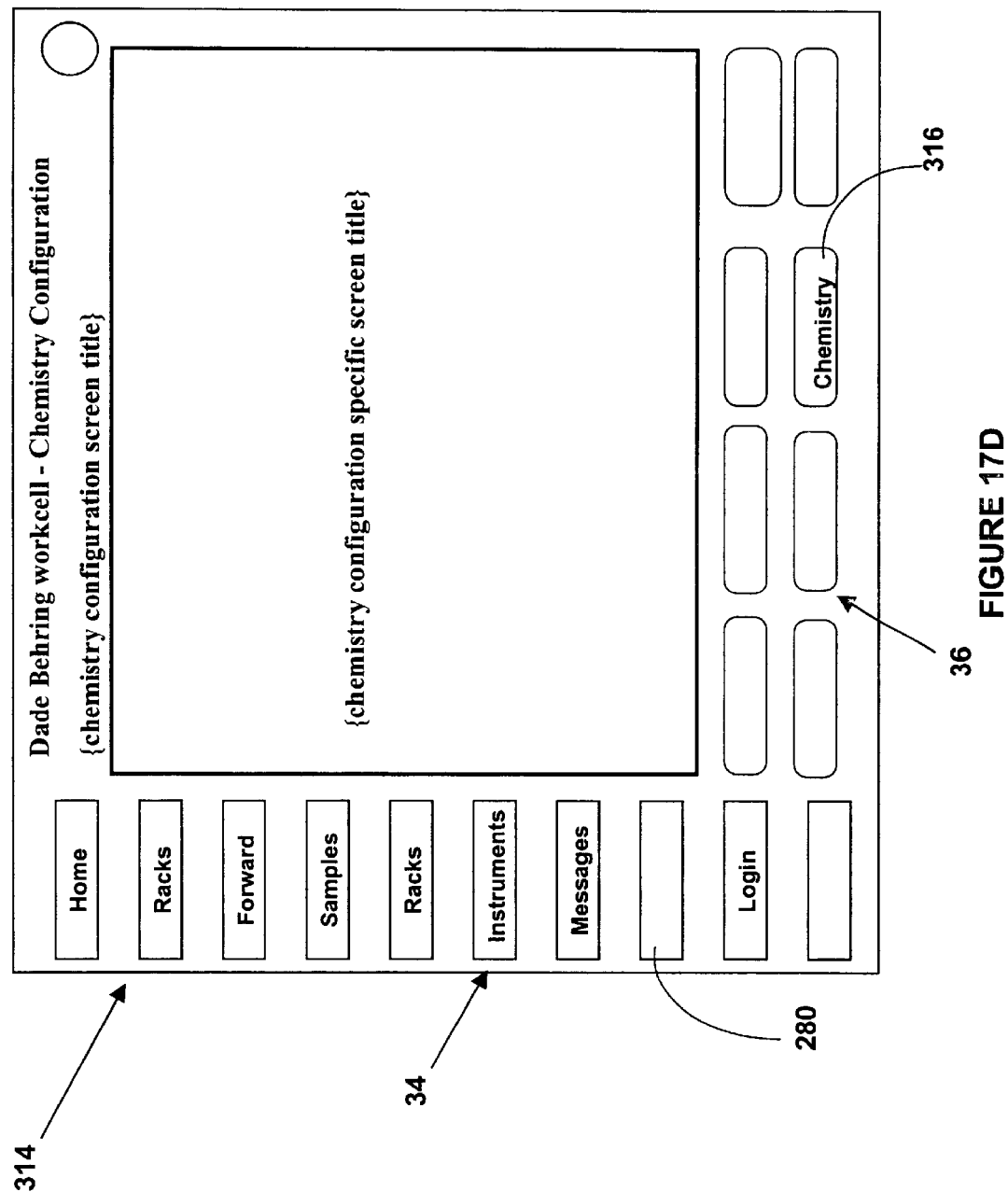
FIG. 17D is a typical representation of the computer interface module information display screen of FIG. 2 further illustrating assay chemistry configuration information exemplary of the present invention and, FIG. 18 is a typical representation of the computer interface module information display screen of FIG. 2 further illustrating a login process exemplary of the present invention.

FIG. 17C shows an Analyzer Configuration screen 310 adapted within CIM 24 to display the operating configuration details of a specific analyzer 12 that may be readily accessed by selecting an Analyzer button 312 from among the group of function specific buttons 36. Operating configuration details include information such as assay menu, reagent inventories, standard and control readings, incubation temperatures, throughput, etc.

FIG. 7D shows an Chemistry Configuration Selection screen 314 adapted within CIM 24 to display the assay and reagent operating configuration details associated with a specific assay on analyzer 12 that may be readily accessed by selecting a Chemistry button 316 from among the group of function specific buttons 36.

Figure 18:
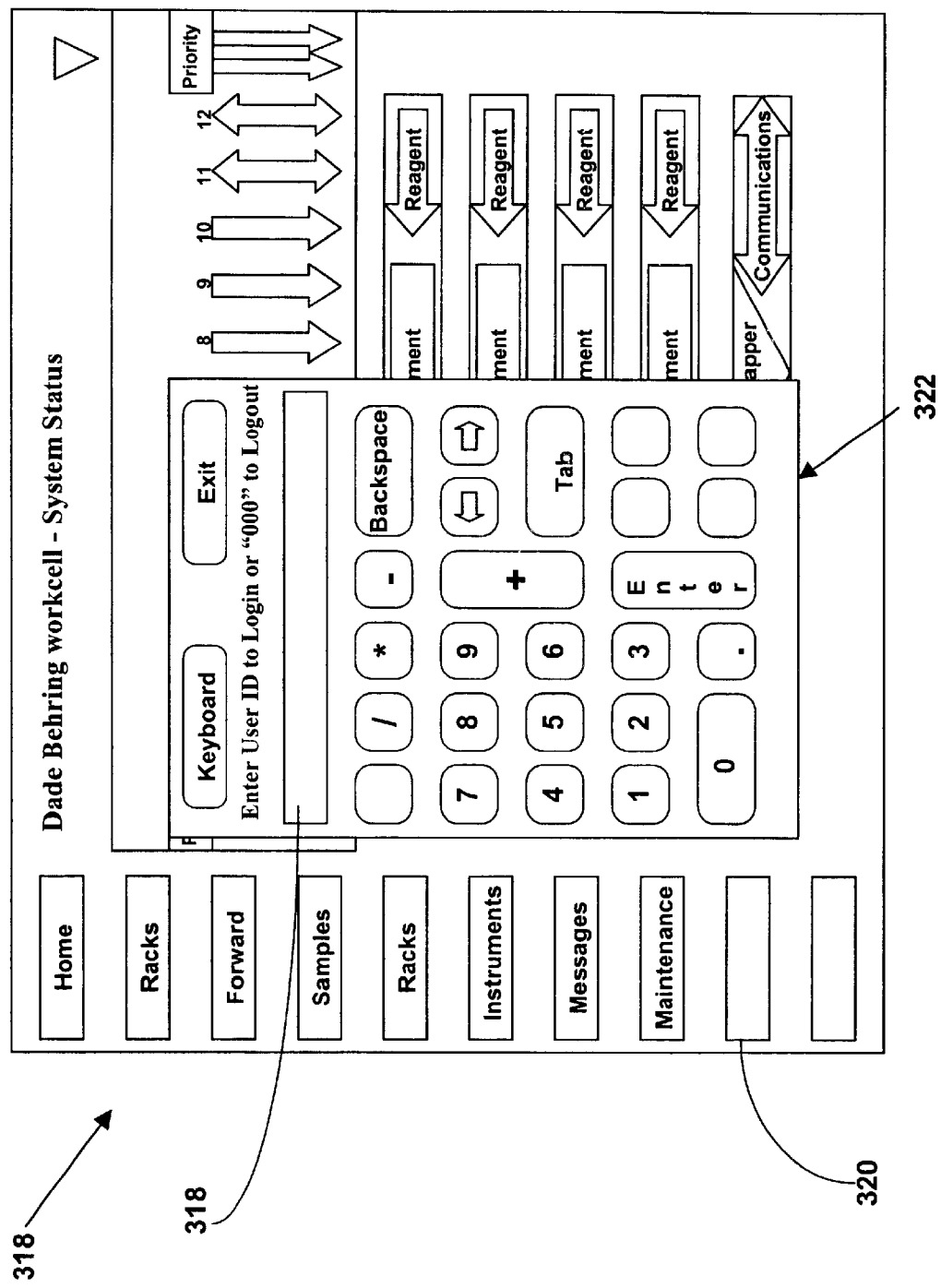

FIG. 18 shows an Login screen 318 adapted within CIM 24 and overlaid on FIG. 7, for example, to invoke restrictions that may exist requiring that a user identify themselves to the CIM 24 and then possess specific privileges.

When a button identified as Login 320 is pressed a numeric keyboard 322 will be rendered to facilitate user ID entry. Upon accurate and authorized completion of a "Login" panel 324, the screen will be restored its previous state. The user can also use this "Login" function to Logout from the system. To Logout the user enters all zeros (000) at the Login prompt.

Those skilled in the art will appreciate that the embodiments of the invention disclosed herein are illustrative of the principles of the invention and that other modifications may be employed which are still within the scope of the invention. For example, obvious variants of the invention would also be applicable to a multi-device system having a larger number of different types of automated analyzers and sample preparation devices with a few adjustments to the parameters. The method also could be easily extended to include detailed specific information display screens related to maintenance or quality control activities. In another embodiment, the Accordingly, the present invention not limited to those embodiments precisely shown and described in the specification but only by the following claims.

What is claimed is:

1. A computer interface display module adapted to facilitate interactions between an operator and an automated clinical analytical system wherein the module comprises a visual touch screen adapted to display a menu including icons, scroll bars, boxes and buttons through which the operator may interface with said clinical analytical system and wherein said menu comprises a number of function buttons programmed to display functional aspects of said clinical analytical system and further comprises a number of function specific buttons programmed to display functional aspects of said function buttons so that detailed information about the clinical analytical system may be displayed by activating no more than two of said function buttons and function specific buttons.

2. The module of claim 1 wherein the clinical analytical system comprises a plurality of interrelated sample preparation devices adapted to prepare a biological sample for sample analysis and a plurality of automated clinical analyzers adapted to analyze said biological sample.

3. The module of claim 2 wherein the function buttons access information about individual analyzers or sample preparation devices or sample transfer devices.

4. The module of claim 3 wherein the function specific buttons access information about processing status of the analyzer and sample preparation devices and display a color coding of the clinical system's main components as described by yellow if the clinical system is low on consumables used in sample handling or analysis, red if out of consumables, and green for all other conditions.

5. The module of claim 3 wherein the function specific buttons access information about a processing status of the analyzer and display a color coding of the analyzer's main components as described by yellow if an analysis submodules is unavailable, red if in an error state, green for all other conditions.

6. The module of claim 3 wherein the function specific buttons access information about the processing status of the analyzer and display a color coding of the analyzer's reagent status as described by yellow if getting low on reagent, red if out of any reagent, green for all other conditions.

7. The module of claim 3 wherein the function specific buttons access information about the status of the sample preparation devices as described by the status of the various components and/or component groups in the sample preparation device as may be required for the different sample preparation operations such as decapping of a closed sample tube, aliquotting of portions of samples from a primary tube to a secondary tube, sample identification, dilution, centrifugation, etc, in order to prepare the original biological sample for analysis by the analyzer.

8. The module of claim 6 wherein the information about individual analyzers within the clinical analytical system includes all messages for all analyzers, messages pertaining to an aliquot portion of all analyzers, messages pertaining to an analysis portion of all analyzers, messages pertaining to a reagent inventory on all analyzers, messages pertaining to low reagent inventory on all analyzers, and a time and date when analyzer information was last changed.

9. The module of claim 6 wherein information about individual analyzers includes an operating manual configuration details such as assay menu, reagent inventories, standard and control readings, incubation temperatures, throughput, a list of System Setup screens, and information that is useful in making a operational diagnostic evaluation before or during routine quality control procedures.

10. The module of claim 2 wherein the function buttons access information about individual samples or racks of samples being analyzed by said analyzers or being prepared for analysis by said sample preparation devices.

11. The module of claim 10 wherein the function specific buttons access information about an identifier, a locator and a processing status of individual biological samples or racks of biological samples being analyzed by said analyzers or being prepared for analysis by said sample preparation devices.

12. The module of claim 5 wherein the processing status of individual biological racks includes information such as the rack is empty, status is unknown, is an input rack waiting for unloading, is currently being unloaded, is an output rack and waiting for loading, is currently being loaded, contains some sample(s) that do not have all the test results for tests ordered on the clinical analytical system reported, all samples in the rack have completed tests ordered, was last used as an output rack and is no longer on the system, is a sorted output rack and is currently empty waiting for sample tubes to be loaded, is the sorted output rack that is currently being loaded, contains only samples that require further processing outside the clinical analytical system but also contains some sample(s) that do not have all test results for tests ordered on the clinical analytical system reported, contains only samples that require further processing outside the clinical analytical system, or was last used as a sorted output rack and is no longer on the system.

13. The module of claim 11 wherein the processing status of individual biological samples includes information such as priority of processing the sample, an unknown status, pre-analytical processing in progress, analyzer(s) processing in progress, testing complete, test results sent to laboratory information system, a list of all samples on the system, a list of all samples with test results pending, a list of all samples completed on a given day, a list of all samples completed in a given day but results have not been sent to the laboratory information system, list of all samples that have laboratory information system information, but have not been identified at the system, an estimated time for all tests ordered for the sample to be complete, including any required pre-analytical processing time, a test abbreviation for ordered tests, any test results reported by the analyzer, a unit of measure used in reporting the results, and a high and a low result value that are considered normal for ordered tests.

14. The module of claim 1 further including a laboratory information system interfaced to said clinical analytical system through said module.

* * * * *